(12) United States Patent
Wood

(10) Patent No.: US 6,487,442 B1
(45) Date of Patent: Nov. 26, 2002

(54) DETECTION OF ABNORMAL AND INDUCTION OF NORMAL HEAT RATE VARIABILITY

(76) Inventor: Nicholas Wood, 16 Ensign Rd., Rowayton, CT (US) 06853

( * ) Notice: Subject to any disclaimer, the term of this patent is extended or adjusted under 35 U.S.C. 154(b) by 0 days.

(21) Appl. No.: 09/559,653

(22) Filed: Apr. 28, 2000

(51) Int. Cl.$^7$ .............................................. A61B 5/0468

(52) U.S. Cl. ...................................... 600/515; 600/519

(58) Field of Search ................................ 600/513, 515, 600/516, 517, 518, 519

(56) References Cited

U.S. PATENT DOCUMENTS

| | | | |
|---|---|---|---|
| 4,018,219 | A | 4/1977 | Hojaiban |
| 4,312,356 | A | 1/1982 | Sowton et al. |
| 4,453,537 | A | 6/1984 | Spitzer |
| D278,746 | S | 5/1985 | Saynajakangas |
| 4,531,527 | A | 7/1985 | Reinhold, Jr. et al. |
| 4,572,192 | A | 2/1986 | Jackman et al. |
| D287,403 | S | 12/1986 | Kiiski et al. |
| 4,625,733 | A | 12/1986 | Säynäjäkangas |
| 4,827,943 | A | 5/1989 | Bornn et al. |
| 4,862,361 | A | 8/1989 | Gordon et al. |
| 4,883,063 | A | 11/1989 | Bernard et al. |
| 4,960,129 | A | 10/1990 | dePaola et al. |
| 5,042,497 | A | 8/1991 | Shapland |
| 5,058,597 | A | 10/1991 | Onoda et al. |
| 5,078,133 | A | 1/1992 | Heinz et al. |
| 5,226,425 | A | 7/1993 | Righter |
| 5,265,617 | A | 11/1993 | Verrier et al. |
| 5,419,338 | A | 5/1995 | Sarma et al. |
| 5,437,285 | A | 8/1995 | Verrier et al. |
| 5,462,060 | A | 10/1995 | Jacobson et al. |
| 5,522,854 | A | 6/1996 | Ideker et al. |
| 5,560,368 | A | 10/1996 | Berger |
| 5,560,370 | A | 10/1996 | Verrier et al. |
| 5,718,235 | A | 2/1998 | Golosarsky et al. |
| 5,873,369 | A | 2/1999 | Lanido et al. |
| 5,891,044 | A | 4/1999 | Golosarsky et al. |

FOREIGN PATENT DOCUMENTS

| | | |
|---|---|---|
| SU | 1607808 A1 | 11/1990 |
| SU | 1683679 A1 | 10/1991 |
| SU | 1769894 A1 | 10/1992 |
| WO | 8809146 | 12/1988 |
| WO | 9406350 | 3/1994 |
| WO | 9602185 A1 | 2/1996 |

OTHER PUBLICATIONS

"The Functional Model Regulation Homeokinesis of Heart Rhythm;" Golosarsky B., research worker, Odessa Research Institute of Medical Rehabilitation (1989).

Malik, Farrell, Cripps, Camm, Heart Rate Variability in Relation to Prognosis After Myocardial Infarction: Selection of Optimal Processing Techniques. *Eur. Heart J.* 1989;10:1060–1074.

(List continued on next page.)

*Primary Examiner*—Scott M. Getzow
(74) *Attorney, Agent, or Firm*—Stevens, Davis, Miller & Mosher, LLP

(57) ABSTRACT

An apparatus and method for predicting potentially fatal arrhythmias up to twenty four hours in advance of the event by employing formulas indicating either too little or too much heart rate variability. A number of these formulas have both predetermined upper and lower limits, which if exceeded for a period of time are a predictor of a potentially fatal arrhythmia. When a patient's ALARM condition is predicted, whether the patient is indoors or outdoors, conscious or unconscious, a redundant protocol is utilized to relay that ALARM condition to a central monitoring station. The central monitoring station informs the patient's doctor, and then uses what ever means are available to transport the patient to the nearest emergency room for treatment. An apparatus and method for pacing the heart in a natural way, once a potentially fatal arrhythmia has been predicted is also disclosed.

42 Claims, 22 Drawing Sheets

OTHER PUBLICATIONS

Malik, Xia, Odemuyiwa, Staunton, Poloniecki, Camm, Influence of the Recognition Artefact in the Automatic Analysis of Long–term Electrocardiograms on Time–domain Measurement of Heart Rate Variability, *Med. Biol. Eng. Comput.* 1993;31:539–544.

Malik, Camm, Components of Heart Rate Variability: What They Really Mean and What We Really Measure, *Am. J. Cardiol.* 1993; 72:821–822.

Malik, Cripps, Farrell, Camm,. Prognostic Value of Heart Rate Variability After Myocardial Infarction: A Comparison of Different Data Processing Methods, *Med. Biol. Eng. Comput.* 1989;27:603–611.

Malik, Camm, Heart Rate Variability and Clinical Cardiology, *Br. Heart J.* 1994; 71:3–6.

Malik, Camm. Significance of Long–term Components of Heart Rate Variability for the Further Prognosis After Acute Myocardial Infarction, *Cardiovasc. Res.* 1990;24:793–803.

Fei, Malik, Short– and Long–term Assessment of Heart Rate Variability for Postinfarction Risk Stratification, In: Malik, Camm, eds, *Heart Rate Variability*, Armonk, NY: Futura; 1995: 341–346.

Heart Rate Variability Standards of Measurement, Physiological Interpretation, and Clinical Use, Circulation, vol. 93, No. 5 (Mar. 1, 1996).

Wood, N.B. "The Prediction of a Potentially Fatal Cardiac Event in the Next 2 to 24 Hours and the Prediction of a Myocardial Infarction Related Death or Sudden Death", Computers in Cardiology conference proceedings (Sep. 24–26, 2001).

Schmidt, Georg, et al "Heart–Rate Turbulence after Ventricular Premature Beats as a Predictor of Mortality After Acute Myocardial Infarction", The Lancet, vol. 353, Issue 9162, p. 1390(1), (Apr. 24, 1999).

de Bruyne, Martine C., et al "Both Decreased and Increased Heart Rate Variability on the Standard 10–Second Electrocardiogram Predict Cardiac Mortality in the Elderly: The Rotterdam Study", American Journal of Epidemiology, vol. 150, No. 12, pp. 1282–1288 (Dec. 15, 1999).

Ziegler, D., et al "Normal Ranges and Reproducibility of Statistical, Geometric, Frequency Domain, and Non–Linear Measures of 24–Hour Heart Rate Variability", Horm Metab Res Issue 12, pp. 672–679 (Dec. 31, 1999).

Pinar, Eduardo, et al "Effects of Verapamil on Indexes of Heart Rate Variability After Acute Myocardial Infarction", The American Journal of Cardiology, vol. 81, Issue 9, pp. 1085–1089 (May 1, 1998).

Deligiannis, Asterios, et al "Effects of Physical Training on Heart Rate Variability in Patients on Hemodialysis", The American Journal of Cardiology, vol. 84, Issue 2, pp. 197–202 (Jul. 15, 1999).

Hayano, Junichiro et al "Prognostic Value of Heart Rate Variability During Long–Term Follow–Up in Chronic Haemodialysis Patients with End–Stage Renal Disease", Nephrology Dialysis Transplantation, vol. 14, Issue 6, pp. 1480–1488 (Jun. 1999).

Lotze, Ulrich, et al "Cardiac Sympathetic Activity as Measured by Myocardial 123–I–Metaiodobenzylguanidine Uptake and Heart Rate Variability in Idiopathic Dilated Cardiomyopathy", The American Journal of Cardiology, vol. 83, Issue 11, pp. 1548–1551 (Jun. 1, 1999).

Ho, Kalon K.L. et al "Predicting Survival in Heart Failure Case and Control Subjects by Use of Fully Automated Methods for Deriving Nonlinear and Conventional Indices of Heart Rate Dynamics" Circulation, vol. 96, pp. 842–848 (1997).

Mäkikallio, Timo H., et al "Heart Rate Dynamics Before Spontaneous Onset of Ventricular Fibrillation in Patients with Healed Myocardial Infracts", The American Journal of Cardiology, vol. 83, pp. 880–884 (Mar. 15, 1999).

Reardon, M., et al "Changes in Heart Rate Variability With Age", Pacing Clin. Electrophysiol., vol. 11., Part 2, pp. 1863–1866 (Nov. 1996)(Abstract).

Skinner, J.E., et al "New Non–Linear Algorithms for Analysis of Heart Rate Variability; Low Dimensional Chaos Predicts Lethal Arrhythmias", Nonlinear Analysis of Physiological Data, Springer, pp. 129–166 (1998).

Fauchier, Laurent et al. "Prognostic Value of Heart Rate Variability for Sudden Death and Major Arrhythmic Events in Patients with Idiopathic Dilated Cardiomyopathy", Journal of American College of Cardiology, vol. 33, No. 5, pp. 1203–1207 (Apr. 1999).

Cheng, T.O. "Decreased Heart Rate Variability as a Predictor for Sudden Death was Known in China in the Third Century A.D.", European Heart Journal, vol. 21, Issue 24, pp. 2081–2082 (Dec. 2000).

Soejima, Kyoko et al. "Age–Adjusted Heart Rate Variability as an Index of the Severity and Prognosis of Heart Failure", Japanese Circulation Journal, vol. 64, pp. 32–38 (Jan. 2000).

Reardon, Michael et al. "Changes in Heart Rate Variability with Age" Pace, vol. 19, pp. 1863–1866 (Nov. 1996).

Makikallio, Timo H. et al. "Prediction of Sudden Cardiac Death by Fractal Analysis of Heart Rate Variability in Elderly Subjects", Journal of the American College of Cardiology, vol. 37, No. 5, pp. 1395–1402 (Apr. 2001).

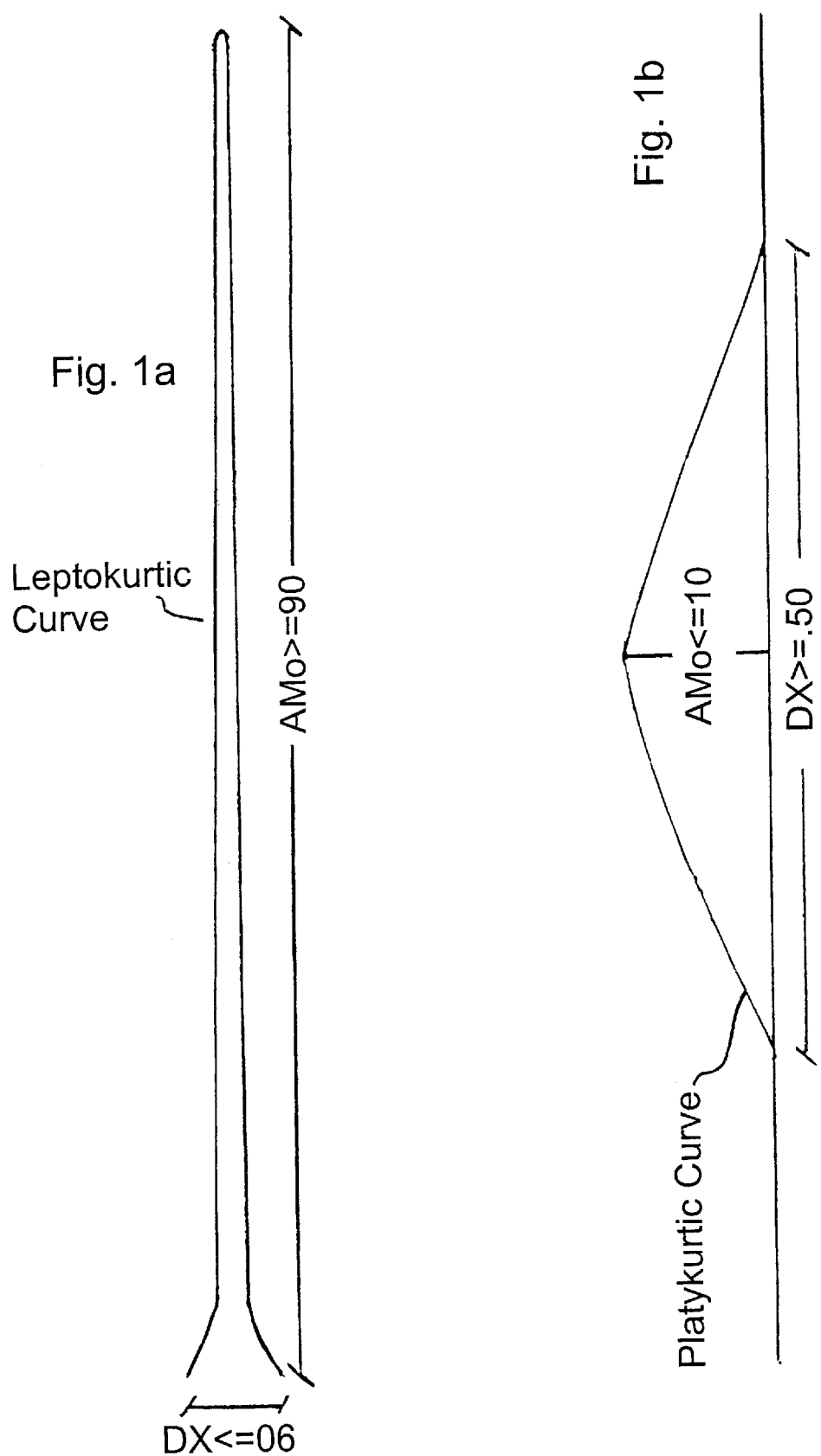

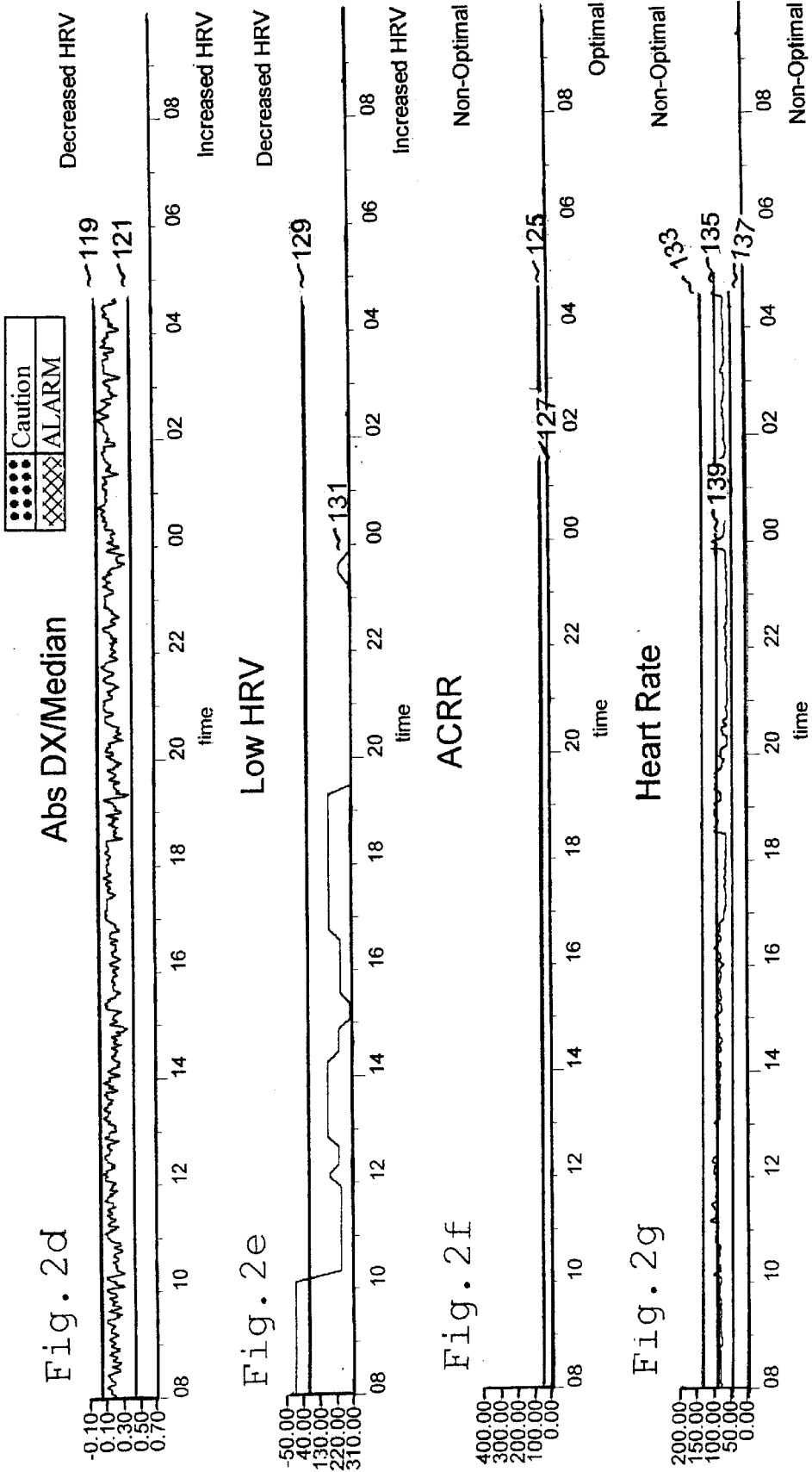

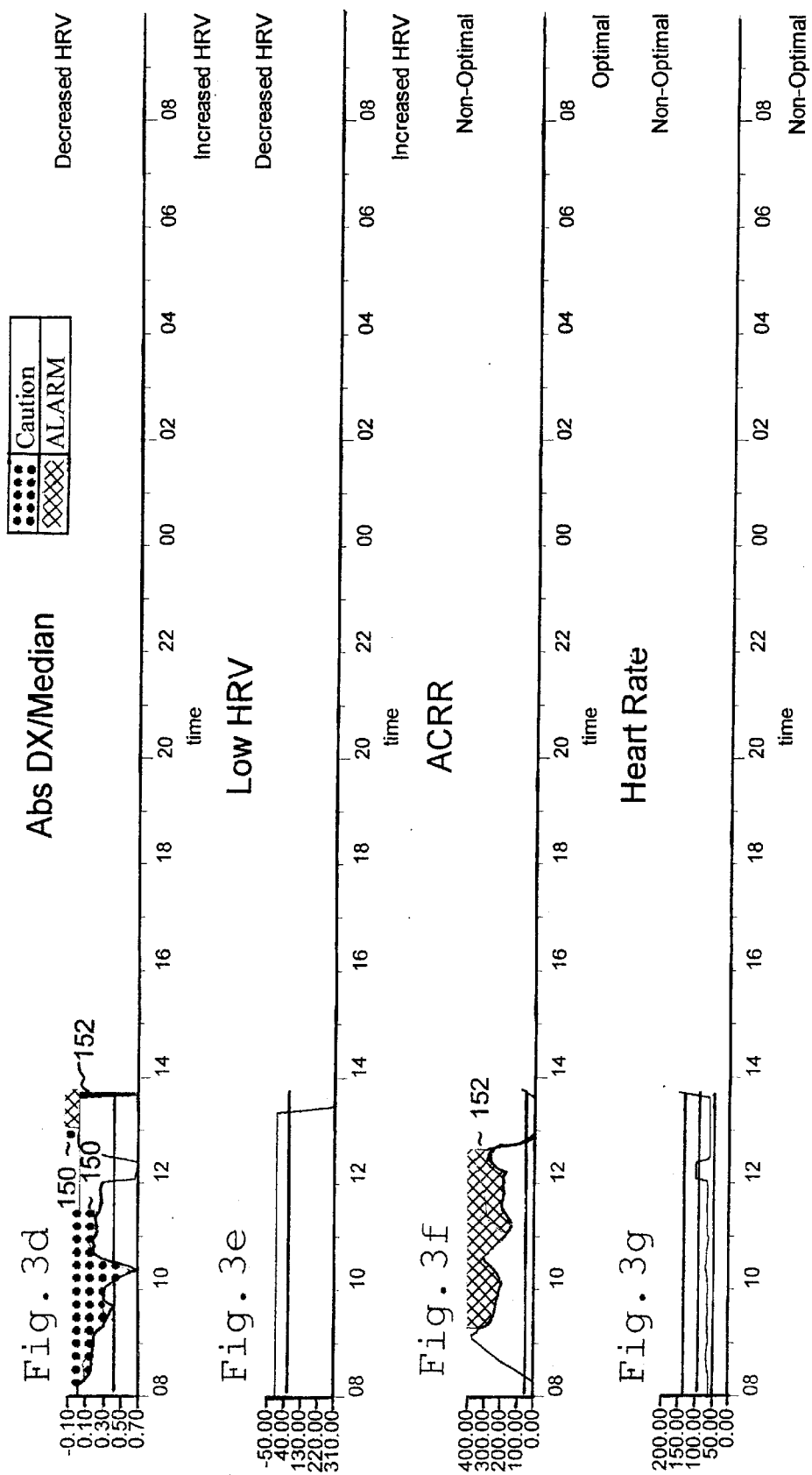

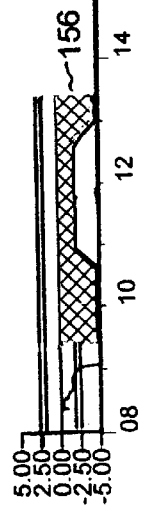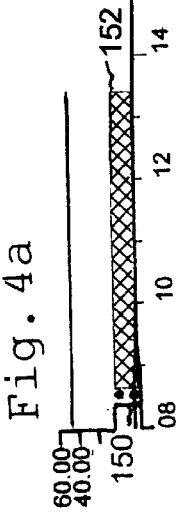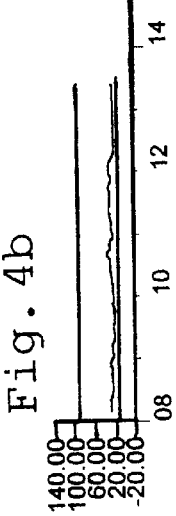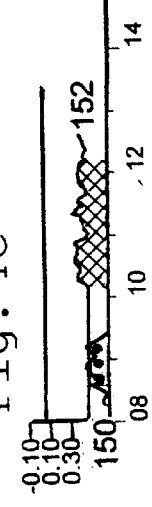

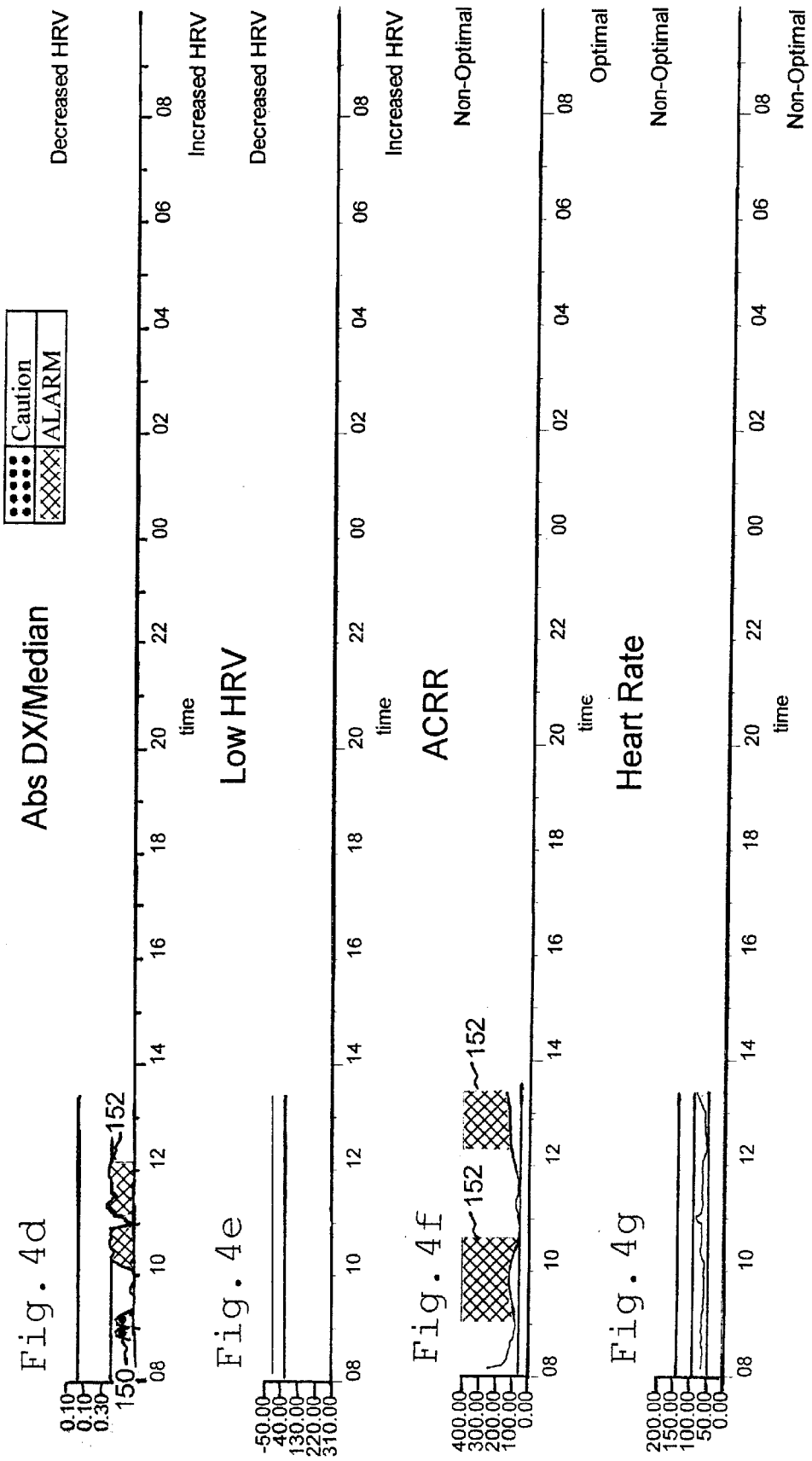

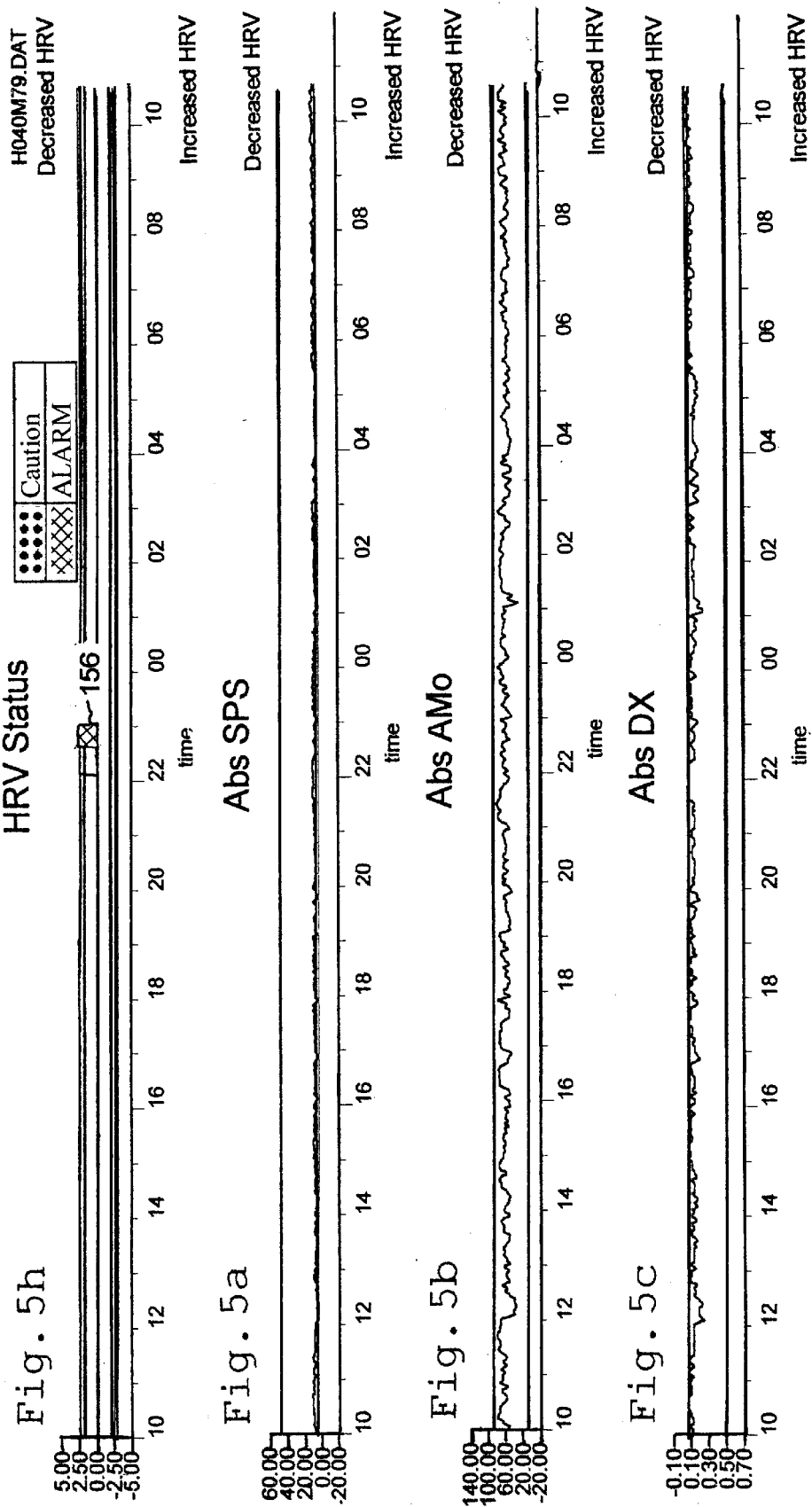

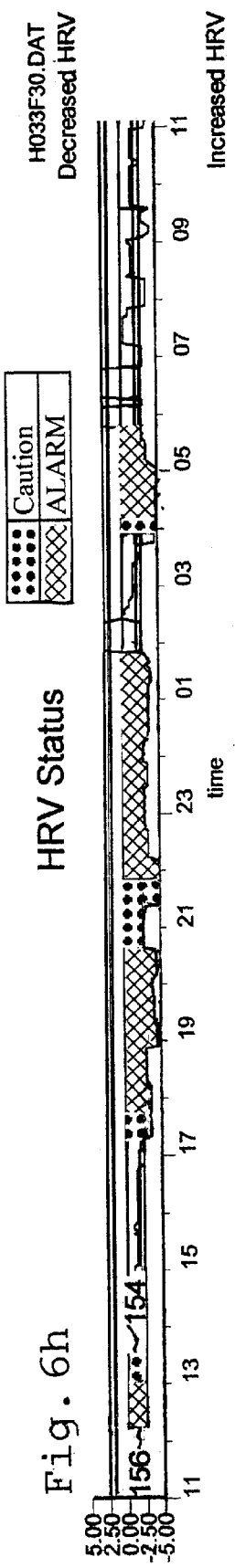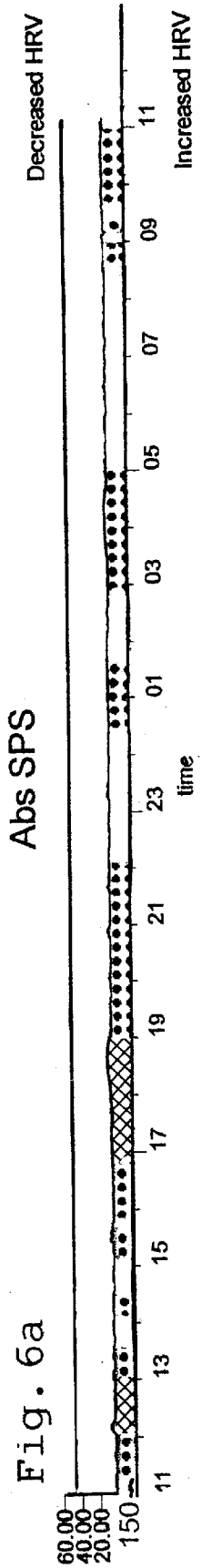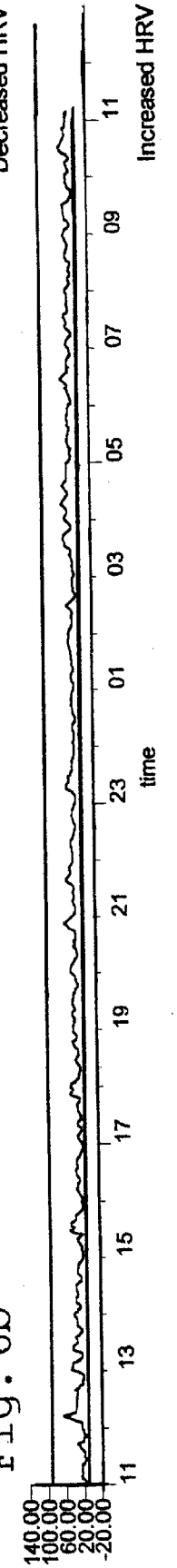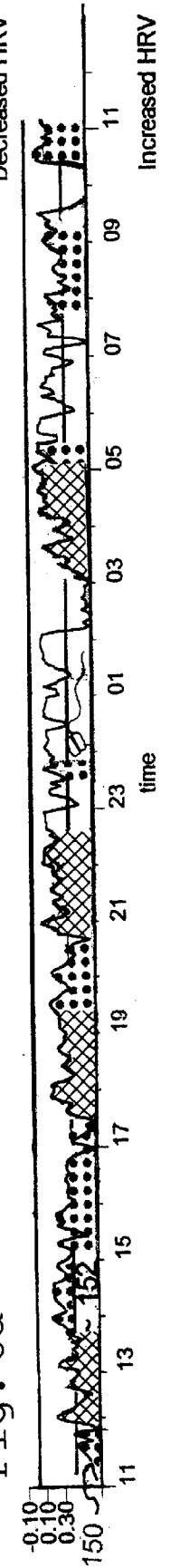
Fig. 6h
Fig. 6a
Fig. 6b
Fig. 6d

Fig. 9c

THIS PAGE INTENTIONALLY LEFT BLANK

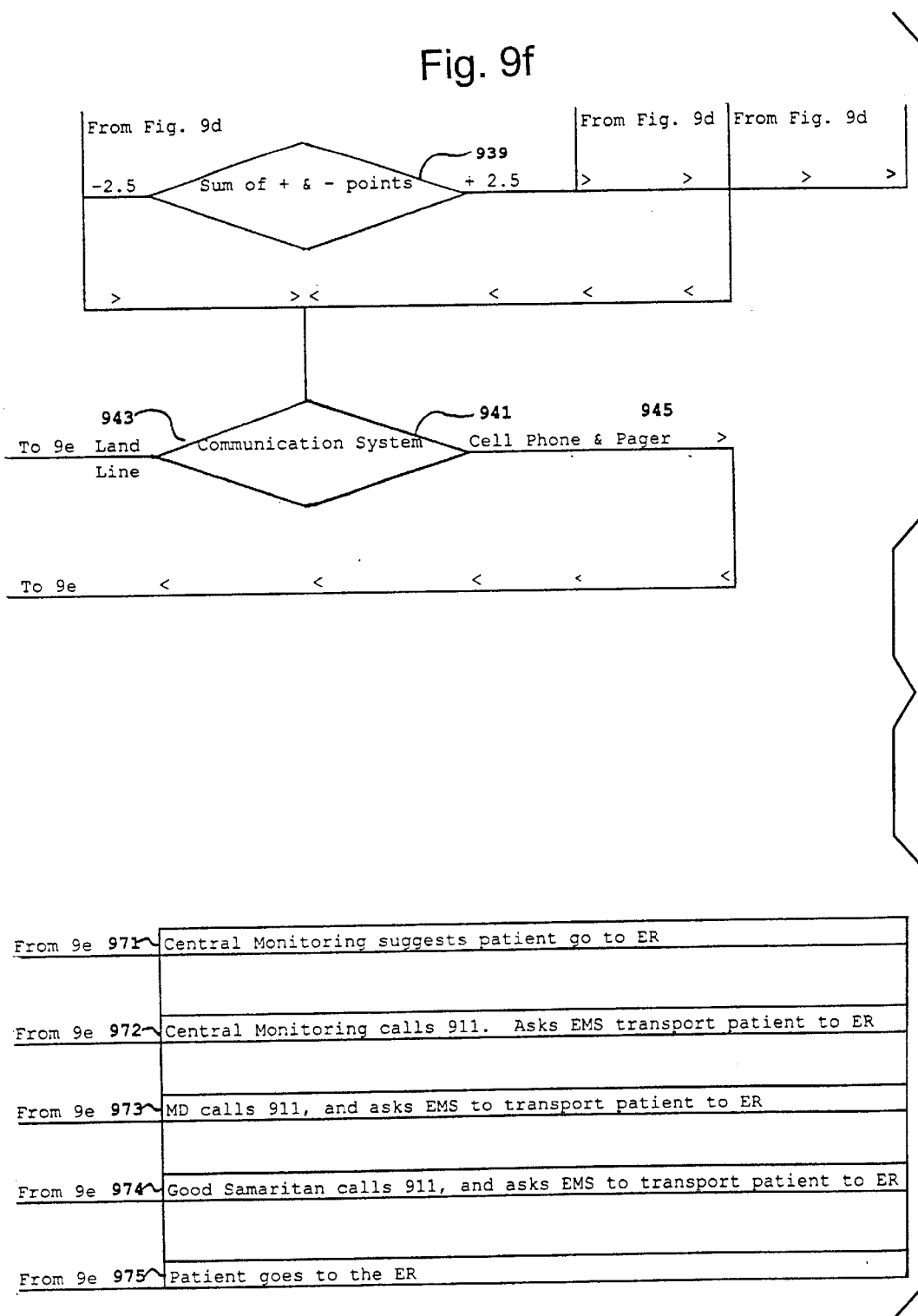

DETECTION OF ABNORMAL AND INDUCTION OF NORMAL HEAT RATE VARIABILITY

BACKGROUND OF THE INVENTION

1. Field of the Invention

The normal heart rate is slightly irregular. Generally, normal irregularity of the heart rate reflects the permanent adaptation of the human body to the environment. In this context the first sign of an impaired heart rate is either a persistent increase or a persistent decrease in the variability of the heart's rate. Sometimes the change in the heart rate alternates between increases and decreases in the variability of the heart's rhythm, and vice versa. Prolonged increases, or decreases, and combinations thereof, can lead to cardiac adverse events ranging from non-sustained ventricular tachycardia to cardiac arrest.

It is believed the variability of the heart rate is controlled by two branches of the autonomic nervous system; the sympathetic branch and the parasympathetic branch. The sympathetic branch increases the heart rate. Its prime function is to prepare the body for stress, the so-called "fight or flight response." The parasympathetic branch decreases the heart rate as when eating or sleeping.

This invention relates to the detection of normal and abnormal heart rate variability and the induction of normal heart rate variability. More particularly, the invention relates to methods and apparatus for the detection of a patient's heart rate variability that we believe is indicative of a patient's sympathetic/parasympathetic stress balance, or distress imbalance.

The invention also relates to heart monitoring devices used by individuals monitored in hospital intensive care units; by patient's after discharge from a hospital intensive care unit; and by patients when exercising to let them know that their stress state is optimal for conditioning their bodies.

The invention further relates to control of a pacemaker or cardioverter defibrillator with a pacemaker so that when the patient's heart rate is abnormal and distressful, according to the invention, a pacemaker or cardioverter defibrillator with a pacemaker induces a heart rate with a pseudo-normal or patient recorded variability for each particular patient.

The invention still further relates to a pacemaker that induces pseudo-normal or patient recorded heart rate variability.

2. Background Description

In the Soviet Union, Rhythmography, that is the study of normal and abnormal variations in the heart, was utilized extensively to determine the condition of individuals and their stress state. This was particularly true of cosmonauts. It was determined, for example, that the heart rate variability of a conditioned athlete is much greater than that of person with coronary disease. That is, the histogram of heart rate variation of a well conditioned athlete exhibits a broad range of variability in the Time Intervals between heart beats and a low relative Amplitude of the Mode. That is the highest number of Time Intervals recorded in a series of Time Intervals. The histogram of a person with a coronary disease exhibits a narrow range of variability and a high relative Amplitude of the Mode, that is the peak of the histogram.

Boris Golosarsky, previously received two patents in the Soviet Union, namely SU-1683679 and SU-1769894. SU-1683679 is for an apparatus, which enables a physician to determine the arithmetic Mean, the Mode, the relative Amplitude of the Mode, and the range of variability of a subject. In the second patent in the Soviet Union, SU-1769894, he disclosed how these measurements may be utilized together with electrosleep to treat post myocardial infarction e.g., heart attack patients.

GW Scientific, Inc. measured a patient's heart rate variability in relation to the patient's baseline heart variability using mathematical constructs such as UV, AMo, and DX, all as described in U.S. Pat. No. 5,718,235, incorporated herein by reference in its entirety.

Polar Electro Oy of Finland has a patented apparatus comprised of a chest strap with a two lead ECG signal sensor and transmitter, which transmits the heart beat Time Intervals to a wrist mounted unit that can be conveniently used in this invention. See U.S. Pat. Nos. 4,625,733; Des. 278, 746; and Des. 287,403, all incorporated herein by reference in their entirety.

Pulse sensors of various types may also be used to detect the Time Interval between heart beats, (Start-of-Systole to Start-of-Systole, SOS), is essentially equal to the Time Interval between RR peaks in an electrocardiogram, (ECG).

Additional background information is disclosed by Baevsky, R. M., Kirillow, O. I., Kleckin, C. Z., (1984), *Mathematical Analysis of Stress Changes in Heart Rhythm*, Moscow, Academy of Science, USSR.

Schmidt et al, "Heart-rate Turbulence After Ventricular Premature Beats As a Predictor of Mortality After Acute Myocardial Infarction," Lancet Apr. 24, 1999; 353 (9162) :1390–6, relates to ACRRs. This article discloses a formula for predicting myocardial infarction 21 to 24 months in advance. In contrast, the present invention predicts up 24 hours in advance. The formula in this article is quite different from those employed in the present invention.

SUMMARY OF THE INVENTION

Definitions

TABLE A shows there are five abnormal predictive markers, which are comprised of two continuums, the Heart Rate Variability continuum and the Heart Rate continuum, as well as Erratic Variability. The Heart Rate Variability continuum has, as its extremes, high and low variability. The Heart Rate continuum has, as its extremes, bradycardia and tachycardia. Erratic Variability, is comprised of Premature Ventricular Contractions (PVCs) and Atrial Fibrillation (A-Fib). TABLE A lists the parameters in each continuum Values for these parameters are calculated by formulas and compared with values which are considered normal and values which are considered abnormal as explained in the specification. These parameters in TABLE A are also labeled by reference numerals and these reference numerals may be employed elsewhere in the specification when discussing the parameters.

TABLE A

| HEART RATE VARIABILITY CONTINUUM | | |
|---|---|---|
| High Variability dispersion of heart beats | Normal | Low Variability centrality of heart beats |
| Absolute SPS(1) | Normal | Absolute SPS(2) |
| Absolute AMo(3) | Normal | Absolute AMo(4) |
| Absolute DX(5) | Normal | Absolute DX(6) |
| Absolute DX/Median(7) | Normal | Absolute DX/Median(8) |
| | | Low HRV(9) |
| | | 2.0 Caution > 2.5 |
| | | ALARM(10) |

TABLE A-continued

HEART RATE CONTINUUM

| bradycardia(11) | Normal | tachycardia(12) |
|---|---|---|

ERRATIC VARIABILITY

ACRR(13)
PVCs & A-Fib

Data sources: ECG (RR) Time Intervals or pulse wave Start-of-Systole to Start-of-Systole (SOS) Time Intervals from the hardware sources discussed elsewhere. (Note: RR and SOS Time Intervals are used interchangeably to indicate the Time Interval between heart beats. 60 seconds divided by the Time Interval in seconds equals beats per minute, bpm.)

Time Interval: A Time Interval is the duration of time between heart beats, or RR peaks, preferably measured to an accuracy of 20 milliseconds, 0.02 seconds. The accuracy of the Time Interval can range from 15 milliseconds to 30 milliseconds.

Time Segment: A Time Segment is a series of Time Intervals, which can vary in length from 51 Time Intervals to 301 Time Intervals. The preferred default setting is 101 Time Intervals. Typically, from this 101 Time Intervals, up to about 6 outliers are removed.

The time between each heart beat is designated an RR Time Interval. RR Time Intervals are then divided into three subsets as shown in TABLE B.

TABLE B

| RR Time Intervals (milliseconds) | | |
|---|---|---|
| NN | ACRR | MARR |
| 75 to 125 | 1 to 74 and/or 126 to 169 | 0 and/or 170+ |

(Normal-to-Normal): Normal-to-Normal means a normal Time Interval between an RR peak. NN Time Intervals are used to calculate twelve of the thirteen predictive markers. NN equals 75 to 125 milliseconds.

ACRR (Abnormal Cardiac RR): Abnormal Cardiac RR means when the present Time Interval differs from the previous Time interval by +25% or −25%, and this situation occurs 50 or more times while accumulating a Time Segment of 101 NN Time Intervals, then this Time Segment is an ACRR Time Segment. If this condition persists for 52 minutes, or longer, then this is either a +2.5 or −2.5 point ALARM, as influenced by the results of "Absolute SPS" through "2.0 Caution>2.5 ALARM" formulas, the first 10 formulas, for the parameters as set forth below. ACRRs are comprised of Premature Ventricular Contractions (PVCs), and Atrial Fibrillation (A-Fib). ACRRs equal intervals of 1 to 74 milliseconds, and/or 126 to 169 milliseconds.

MARR (Motion Activated RR): Motion Activated RR means some sort of motion influenced the Time Interval between the RR peaks. MARRs equal intervals of Zero and/or 170+ milliseconds.

Outliers are typically the three shortest and the three longest Time Intervals in a 101 NN Time Interval, Time Segment, and are discarded after ACRRs are removed from the Time Segment, and before calculations are made of the other 12 predictive markers.

Non-Stationarity: If the Median and the Mode differ from each other in a 101 Time Interval Time Segment by 20% or more, than this is a case of non-stationarity and the values generated are discarded and not included in any calculations.

The following 10 formulas are for parameters all related to heart rate variability, HRV. The ALARM trigger points and the number of Time Segments the ALARM condition is present are for patients 55 years and older.

Absolute Sympathetic/Parasympathetic Stress (ABS.SPS): Sympathetic/Parasympathetic Stress is determined by the formula:

$$SPS = \sqrt{(0.5/DX)^2 + (AMo/10)^2}$$

In a Time Segment of 95 NN Time Intervals (101 NN Time Intervals minus 6 outliers), if SPS equals or exceeds 48 for any 25 Time Segments out of 50 Time Segments, then this is a +2.5 point ALARM. In a Time Segment of 95 NN Time Intervals, if SPS is between 47 and 3.0, then this is normal condition. In a Time Segment of 95 NN Time Intervals, if SPS equals or is less than 2.5 for any 25 Time Segments out of 50 Time Segments, then this is a −2.5 point ALARM (Parameters 1 and 2 of TABLE A).

Absolute AMo (ABS.AMo): Amplitude of the Mode is the largest number of identical Time Intervals occurring in the Mode of a Time Segment, (e.g. 70 for 70 Time Intervals out of 95 Time Intervals.)

In a Time Segment of 95 NN Time Intervals, if AMo, the most frequent heart rate, occurs 90 times or more for any 25 Time Segments out of 50 is a 2.5 point ALARM. In a Time Segment of 95 NN Time Intervals, if the average rate occurs between 11 through 94 times is Normal. In a Time Segment of 95 NN Time Intervals, if AMo the most frequent heart rate occurs 10 times or less for any 25 Time Segments out of 50, then this is a −2.5 point ALARM. (Parameters 3 and 4 of TABLE A).

Absolute DX (Delta X): Delta X is the difference between the longest value for a Time Interval in a Time Segment and the shortest value, after outliers, and ACRRs, if any, have been discarded (e.g. longest equals 0.72 seconds less shortest equals 0.64 seconds=0.08 seconds=Delta X).

In a Time Segment of 95 NN Time Intervals, if the difference, DX, between the longest and the shortest heart rate is 0.06 seconds or less for any 25 Time Segments out of 50 is a +2.5 ALARM. In a Time Segment of 95 NN Time Intervals, if the difference between the longest and the shortest heart rate is between 0.49 through 0.07 seconds is normal. In a Time Segment of 95 NN Time Intervals, if the difference, DX, between the longest and the shortest Time Interval is 0.50 seconds or more for any 25 Time Segments out of 50, then this is a −2.5 ALARM. (Parameters 5 and 6 of TABLE A).

Median (M): The Median is the Time Interval in a Time Segment, in which there are equal number Time Intervals equal to or larger than, and equal to or smaller than the Median Time Interval (e.g. the 47th Time Interval in a 95 Time Interval Time Segment).

Absolute DX/Median (ABS.DX/M): Delta X divided by the Median is a combination of the two markers above, DX and Median.

In a Time Segment of 95 NN Time Intervals, if DX/Median equals or is less than 0.02 for any 25 Time Segments out of 50 is a +2.5 point ALARM. In a Time Segment of 95 NN Time Intervals, if DX/Median is between 0.025 and 0.420 is normal in a Time Segment of 95 NN Time Intervals, if DX/Median equals or exceeds 0.425 for any 25 Time Segments out of 50, then this is a −2.5 point ALARM. (Parameters 7 and 8 of TABLE A).

Low Heart Rate Variability (Low-HRV): Low-HRV is a condition where 100 or more Time Segments, which have a maximum variation 0.62 seconds or lower, with no more than two (2) exceptions, then this condition is a +2.5 ALARM. Low-HRV is a predictive marker of low heart rate variability. (Parameter 9 of TABLE A).

2.0 Caution>2.5 ALARM: If CAUTION or ALARM signals, for the above four conditions (SPS, AMo, DX, and DX/M), exist for 960 minutes with a gap (a lack of a Caution or an ALARM) of no more than 60 minutes, then the +2.0 Caution (calculated as 4 times 0.5 CAUTION points) becomes a +2.5 ALARM. This parameter is a predictive marker of low heart rate variability. (Parameter 10 of TABLE A).

Moreover, a baseline for SPS, AMo, and DX is established between the 10th and 500th Time Segment. Any deviation above 150% or below 50% of the baseline for more than 45 minutes triggers both a Caution and an ALARM of 2.5 points for any one of the three formulas. The preferred baseline time is 24 hours. TABLE C summarizes the parameters for establishing a baseline.

TABLE C

Parameters for triggering a Caution/ALARM after a baseline has been established

| SPS | AMo | DX |
|---|---|---|
| start = 10 Time Segments | start = 10 Time Segments | start = 10 Time Segments |
| end = 500 Time Segments | end = 500 Time Segments | end = 500 Time Segments |
| ALARMhigh = 1.50 points | ALARMhigh = 1.50 points | ALARMhigh = 1.50 points |
| ALARMlow = 0.50 points | ALARMlow = 0.50 points | ALARMlow = 0.50 points |
| CAUTIONhigh = 1.50 points | CAUTIONhigh = 1.50 points | CAUTIONhigh = 1.50 points |
| CAUTIONlow = 0.50 points | CAUTIONlow = 0.50 points | CAUTIONlow = 0.50 points |
| ALARMtime = 45.00 minutes | ALARMtime = 45.00 | ALARMtime = 45.00 |
| CAUTIONtime = 45.00 | CAUTIONtime = 45.00 | CAUTIONtime = 45.00 |

The points assigned to these parameters in TABLE C for these formulas relative to the patient's own baseline may differ from the points attached to these parameters SPS, AMo, and DX when measuring these parameters SPS, AMo, and DX as Abs.SPS, Abs.AMo, and Abs.DX against predetermined upper and lower limits (see Tables 1a–c) as explained elsewhere in this specification.

Moreover, in applying the formula for converting a 2 point CAUTION signal to a 2.5 point ALARM signal the following time periods are employed.

SpecialTime1=60; 60 minutes maximum time after AMo first triggers a Caution that other formulas must also trigger a Caution (SPS, DX, DX/Median). Then the following must occur.

SpecialTime2=960; 960 combined total CAUTION minutes of the formulas (SPS, AMo, DX, DX/Median), for the CAUTIONs to convert to a 2.5 point ALARM, except as set forth below.

GapTimeIndivMax=210; If the combined total of gaps in the four formulas (SPS, AMo, DX, DX/Median), equals or exceeds 210 minutes, then reset to zero. A "gap" is a non-CAUTION status.

GapTimeWindow=60; if a gap occurs in any of the four formulas, (SPS, AMo, DX, DX/Median), that is 60 minutes or longer, then reset to zero.

Heart Rate: If the heart rate is 40 bpm or 135 bpm for more than 45 minutes, then this is –2.5 or +2.5 point ALARM. (Parameters 11 and 12 of TABLE A).

The parameters calculated by the following formulas, "a" through "e" and "f", can be substituted for AMo and/or DX. Typically for each of AMo and/or DX replaced, one or more of parameters "a" through "e" and "f" are substituted.

(a) Standard Deviation Average Normal to Normal, SDANN: SDANN is a measure of the dispersion around the mean of NN Time Intervals in a five minute Time Segment, after ACRRs (Premature Ventricular Contractions and Atrial Fibrillation, if any) have been discarded, according to the formula. A value of 50 or lower in a SDANN Time Segment is a predictive marker of a serious cardiac condition.

$$SDANN = \sqrt{(n\Sigma x)^2 - (\Sigma x)^{2/n(n-1)}}$$

(b) Point Normal to Normal 50 milliseconds, PNN50: PNN50 is a measure of the concentration of Time Intervals at 50 milliseconds or lower during a five minute PNN50 Time Segment. A value of 50 milliseconds or lower in a PNN50 Time Segment is a predictive marker of a serious cardiac condition.

(c) Amplitude of the Median (AM): The Amplitude of the Median is the 47th Time Interval occurring in a Time Segment, e.g. if the 47th Time interval is 0.70 and occurs 21 times, them AM equal 21.

(d) Full Width at Half Maximum (FWHM) The Full Width at Half Maximum is a measure of the dispersion of Time Intervals. The value of Half Maximum is one half of (AMo) or (AM) and the Full Width is the length of a horizontal line (DX) across the vertical line at right angles to the vertical line of (AMo) or (AM) through the point of Half Maximum.

(e and f) Kurtosis: Kurtosis is the description of the Gaussian distribution of data points. A Gaussian curve that is peaked is leptokurtic the vertical height of which is equivalent to AMo, FIG. 1a. A Gaussian curve that is flat is platykurtic the horizontal base of which is equivalent to DX, FIG. 1b.

Another available parameter is:

(g) ANN: Average of the NN values in a Time Segment. When ANN exceeds a predetermined percentage of the baseline values for a predetermined period of time, then a CAUTION or ALARM may be signaled.

Patient: A patient is anyone whose Time Intervals are measured.

OK: The patient's physical condition is normal and not stressed.

Caution: The patient has a potentially unhealthy stress condition.

ALARM: An ALARM is present when the patient's current HRV Status indicates a state of low heart rate variability, or a state of high heart rate variability, or ACRR's, for a predetermined number of Time Segments or a predetermined period of time.

Motion Sensor: A transducer detects a range of motions from, no motion, to slight motion, to moderate motion to heavy motion and over load. No motion for a predetermined period of time and a heart or pulse rate indicates a Comatose ALARM. Slight motion and a heart or pulse rate indicate sleep. Heavy motion indicates exercise and over load (spike) followed by no motion, indicates a fall.

Comatose ALARM: If Time Intervals are detected but no motion is detected for 30 or more minutes, then this is a +2.5 point Comatose ALARM.

Cardiac Arrest ALARM: If no Time Intervals are detected for 15 or more seconds and the galvanic skin response sensor indicates the ECG electrodes or the pulse sensor is in contact with the patient, then this is a +2.5 point Cardiac Arrest ALARM.

Long Term Cardiac Caution: If the heart rate is raised to, for example, 150 bpm, as is sometimes the case during a stress test, and a reading of the patient's heart rate is taken at the end of this strenuous exercise, and a second heart rate reading is taken one minute later, then if the difference between the two heart rates is 12 bpm or less, then the patient has a long term cardiac caution condition. If the heart rate is raised to say an aerobic target heart of, for example, 115 to 130 bpm, and a reading of the patient's heart rate is taken at the end of this aerobic exercise, and a second heart rate reading is taken one minute later, then if the difference between the two heart rates is 8 to 10 bpm or less, then the patient has a long term cardiac caution condition. The patient's functional and stress states may be displayed to the patient or a health care provider in an alphanumeric fashion, utilizing the HRV Status output. This enables the patient or health care provider to determine the patient's stress status substantially instantaneously at any time or place, and to attain a state of effective cardiovascular fitness.

Detection of abnormal heart rate variability in a series of Time Segments can therefore be used to signal a health care provider, or pacemaker, or cardioverter defibrillator with a pacemaker, to intervene according to the invention, or to indicate that the heart is being over stressed by the particular activity (e.g. physical, psychogenic) being engaged in.

Also according to the invention, a pacemaker or a cardioverter defibrillator with a pacemaker can be programmed to provide a normal, therapeutic heart rate variability rather than an unnatural steady beat as in the prior art. This may be accomplished by, (1) recording the patient's normal, variable heart rate, or (2) the normal, variable heart rhythm of an individual most nearly matching the patient's age, sex, race, build and athletic condition, or (3) using a random pulse generator that produces a normal, variable histographic heart rate, all in conjunction with an impedance pacemaker, (a pacemaker that detects respiration).

The details for an apparatus to perform the process aspects of the present invention are provided by U.S. Pat. No. 5,718,235, incorporated herein by reference. See, for example, FIG. 5 of U.S. Pat. No. 5,718,235. However, of course, the apparatus would be modified where necessary to contain a software program to perform the calculations and comparisons to perform the process of the present invention. Also, it could be modified to include interval detectors such as ultrasound doppler sensors, a piezo electric microphone, or any other appropriate sensor.

OBJECTS OF THE INVENTION

It is therefore an object of this invention to provide a method and apparatus for determining the patient's stress state.

Another preferred object of the invention is to provide such apparatus, which allows the patient to exercise in a stress state which will bring about a maximum conditioning effect.

A further preferred object of the invention is to provide such apparatus and method that the patient will be notified of non-optimal or an ALARM or Caution distress state.

Still another preferred object of the invention is to detect stress and distress states from simple parameters derived from the recording of a plurality of durations of successive Time Intervals between heart beats.

Still another preferred object of the invention is to detect cardiac distress.

Still another preferred object of the invention is to detect abnormal heart rate variability over a relatively short period of time and to signal this abnormality to a health care provider, or a pacemaker or a cardioverter defibrillator with a pacemaker, to initiate intervention.

Still another preferred object of the invention is to cause a pacemaker or cardioverter defibrillator with a pacemaker, to pace a heart with a normal heart rate variability.

Other preferred objects of the invention will be apparent from the following disclosure.

The invention accordingly comprises a method comprising several steps and the relation of one or more of such steps with respect to each of the others, and the apparatus embodying features of construction, elements, and arrangements of parts, which are adapted to effect such steps, all as exemplified in the following detailed disclosure.

BRIEF DESCRIPTION OF THE DRAWINGS

For a fuller understanding of the nature and objects of the invention reference should be had to the following detailed description taken in connection with the accompanying drawings in which: the same reference characters refer to the same elements throughout the several views of the drawings.

FIG. 1a shows a plot of a Platykurtic Curve.

FIG. 1b shows a plot of a Leptokurtic Curve.

FIG. 2d shows a plot of Abs DX/Median versus time.

FIG. 2e shows a plot of Low HRV versus time.

FIG. 2f shows a plot of ACRR versus time.

FIG. 2g shows a plot of Heart Rate versus time.

FIG. 3d shows a plot of Abs DX/Median versus time.

FIG. 3e shows a plot of Low HRV versus time.

FIG. 3f shows a plot of ACRR versus time.

FIG. 3g shows a plot of Heart Rate versus time.

FIG. 4a shows a plot of Abs SPS versus time.

FIG. 4b shows a plot of Abs AMo versus time.

FIG. 4c shows a plot of Abs DX versus time.

FIG. 4d shows a plot of Abs DX/Median versus time.

FIG. 4e shows a plot of Low HRV versus time.

FIG. 4f shows a plot of ACRR versus time.

FIG. 4g shows a plot of Heart Rate versus time.

FIG. 4h shows a plot of HRV Status versus time.

FIG. 5a shows a plot of Abs SPS versus time.

FIG. 5b shows a plot of Abs AMo versus time.

FIG. 5c shows a plot of Abs DX versus time.

FIG. 5h shows a plot of HRV Status versus time.

FIG. 6a shows a plot of Abs SPS versus time.

FIG. 6b shows a plot of Abs AMo versus time.

FIG. 6d shows a plot of DX/Median versus time.

FIG. 6h shows a plot of HRV Status versus time.

FIGS. 9a–f show portions of the decision tree diagram.

DETAILED DESCRIPTION OF THE PREFERRED EMBODIMENTS

Figure 2H:
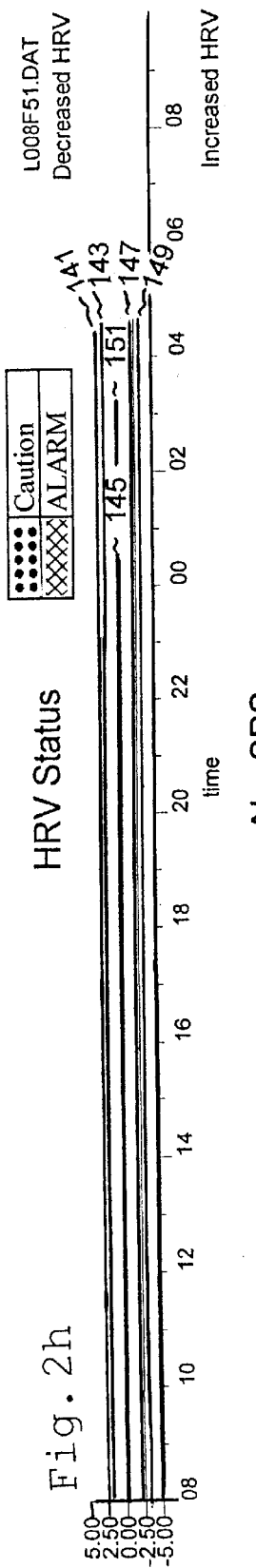
FIG. 2h shows a plot of HRV Status versus time.

The present invention includes analysis of the Kurtosis of patient data. Kurtosis is the degree of peakedness or flatness of a probability distribution, relative to the normal distribution with the same variance. Kurtosis is the description of the Gaussian distribution of data points and involves the concepts of leptokurtic and platykurtic curves.

A leptokuric curve pertains to a probability distribution more heavily concentrated around the mean, i.e., having a sharper, narrower peak, than the normal distribution with the same variance. Moreover, a leptokurtic curve is a Gaussian curve that is peaked and has a vertical height equivalent to AMo as shown in FIG. 1a.

A platykurtic curve of a probability distribution has a broader, flatter peak than the normal distribution with the same variance. Moreover, a platykurtic curve is a Gaussian curve that is flat and has a horizontal base equivalent to DX as shown in FIG. 1b.

A mesokurtic curve (not shown) is normal.

The formula for kurtosis is Formula I as follows:

$$\text{Kurtosis} = (\Sigma(X-\mu)^4 / (N\delta)^4) - 3 \quad \text{I,}$$

wherein $\delta$ is the standard deviation.

In Formula I, the parameter $(\Sigma(X-\mu)^4/(N\,\delta)^4)$ equals $a_4$ defined as in Formula II.

$$a_4 = \frac{\left(\sum_{i=1}^{k}(f_i(X_i - \overline{X})^4 / n)\right)}{s^4}. \quad \text{II}$$

In the Formula II, $a_4=3$ is mesokurtic (normal distribution); $a_4>3$ is leptokurtic; and $a_4<3$ is platykurtic. The formula evolves from a value of 3 down to a definition of DX, and evolves from a value of 3 up to a definition of AMo.

The absolute ALARM settings for DX and AMo are as follows:

Decreased HRV DX ALARM is $\leq 0.06$;

Decreased HRV AMo ALARM is $\geq 90$;

Increased HRV DX ALARM is $\geq 0.5$; and

Increased HRV AMo ALARM is $\leq 10$.

For any person, but especially for an ambulatory person age 18–54, a kurtosis value $(a_4) \geq 30$ is an Increased HRV ALARM. and a kurtosis value $(a_4) \leq 0.3$ is an Decreased HRV ALARM., for a ratio of at least about 28 to 31 out of 50 Time Segments, wherein at least about 30 Time Segments are measured.

A patient's heart rate can be measured and then analysis of the Kurtosis of the heart rate leads to sympathetic and parasympathetic heart parameters which can be employed to predict arrhythmia.

TABLES 1a, 1b and 1c list the names of the parameters and the ranges of predetermined normal values of these parameters. This results in formulas used to predict arrhythmia. TABLES 1a, 1b and 1c list the points assigned to Caution or ALARM conditions recorded. If at any time the points total 2.0 or less, the patient's HRV health is satisfactory. In the calculations up to 3 high outliers and 3 low outliers per Time Segment are permitted.

TABLE 1a

| Names of Parameters Used | Points | Standard Age 18 to 54 (predict) | Standard Age 55+ (predict) | Hi-Risk All Ages (predict) | ER (predict) | Apnea (detect) |
|---|---|---|---|---|---|---|
| (defaults) | | | | | | |
| resolution | | 0.06 | 0.06 | 0.20 | 0.20 | 0.06 |
| outliers (high/low) | | 3 | 3 | 3 | 3 | 3 |
| segment size (intervals) | | 101 | 101 | 101 | 101 | 101 |
| (ABS.SPS.HI) | | | | | | |
| ALARMHIGH | | 48 | 48 | 48 | 48 | 48 |
| ALARMtrigger | +1.0 | 30 | 15 | 560 | 48 | n/a |
| ALARMsegments | | 50 | 50 | 700 | 50 | n/a |
| Cautiontrigger | +0.5 | 5 | 10 | 460 | 45 | n/a |
| Cautionsegments | | 50 | 50 | 700 | 50 | |
| (ABS.SPS.LO) | | | | | | |
| ALARMLOW | | 2.50 | 4.00 | 3.50 | 6.00 | 4.00 |
| ALARMtrigger | −1.0 | 25 | 15 | 35 | 10 | 37 |
| ALARMsegments | | 50 | 50 | 40 | 50 | 50 |
| Cautiontrigger | −0.5 | 15 | 10 | 30 | 9 | 37 |
| Cautionsegments | | 50 | 50 | 40 | 50 | 50 |

TABLE 1a-continued

| Names of Parameters Used | Points | Standard Age 18 to 54 (predict) | Standard Age 55+ (predict) | Hi-Risk All Ages (predict) | ER (predict) | Apnea (detect) |
|---|---|---|---|---|---|---|
| (ABS.AMo.HI) | | | | | | |
| ALARMHIGH | | 90 | 90 | 95 | 95 | n/a |
| ALARMtrigger | +1.0 | 30 | 15 | 575 | 48 | n/a |
| ALARMsegments | | 50 | 50 | 700 | 50 | n/a |
| Cautiontrigger | +0.5 | 15 | 10 | 460 | 45 | n/a |
| Cautionsegments | | 50 | 50 | 700 | 50 | n/a |
| (ABS.AMo.LOW) | | | | | | |
| ALARMLOW | | 10 | 10 | 10 | 10 | n/a |
| ALARMtrigger | −1.0 | 25 | 20 | 7 | 25 | n/a |
| ALARMsegments | | 50 | 50 | 10 | 50 | n/a |
| Cautiontrigger | −0.5 | 15 | 15 | 5 | 20 | n/a |
| Cautionsegments | | 50 | 50 | 10 | 50 | n/a |

TABLE 1b

| | Points | Standard Age 18 to 54 (predict) | Standard Age 55+ (predict) | Hi-Risk All Ages (predict) | ER (predict) | Apnea (detect) |
|---|---|---|---|---|---|---|
| Name of Parameters Used (defaults) | | | | | | |
| resolution | | 0.06 | 0.06 | 0.20 | 0.20 | 0.06 |
| outliers (high/low) | | 3 | 3 | 3 | 3 | 3 |
| segment size | | 101 | 101 | 101 | 101 | 101 |
| (ABS.DX.LO) | | | | | | |
| ALARMLOW | | 0.06 | 0.06 | 0.06 | 0.06 | n/a |
| ALARMtrigger | −1.0 | 25 | 20 | 575 | 48 | n/a |
| ALARMsegments | | 50 | 50 | 700 | 50 | n/a |
| Cautiontrigger | −0.5 | 10 | 15 | 460 | 45 | n/a |
| Caution segments | | 50 | 50 | 700 | 50 | n/a |
| (ABS.DX.HI) | | | | | | |
| ALARMHIGH | | 0.50 | 0.50 | 0.50 | 0.50 | n/a |
| ALARMtrigger | +1.0 | 30 | 15 | 40 | 15 | n/a |
| ALARMsegments | | 50 | 50 | 50 | 50 | n/a |
| Cautiontrigger | +0.5 | 15 | 10 | 35 | 10 | n/a |
| Cautionsegments | | 50 | 50 | 50 | 50 | n/a |
| Name of Formulas Used | | | | | | |
| (ABS.DX/M.LO) | | | | | | |
| ALARMLO | | 0.02 | 0.02 | 0.02 | 0.02 | n/a |
| ALARMtrigger | −1.0 | 25 | 15 | 575 | 48 | n/a |
| ALARMsegments | | 50 | 50 | 700 | 50 | n/a |
| Cautiontrigger | −0.5 | 5 | 5 | 460 | 45 | n/a |
| Cautionsegments | | 50 | 50 | 700 | 50 | n/a |
| (ABS.DX/M.HI) | | | | | | |
| ALARMHIGH | | 0.425 | 0.425 | 0.425 | 0.425 | n/a |
| ALARMtrigger | +1.0 | 25 | 20 | 45 | 20 | n/a |
| ALARMsegments | | 50 | 50 | 50 | 50 | n/a |
| Cautiontrigger | +0.5 | 15 | 15 | 40 | 18 | n/a |
| Cautionsegments | | 50 | 50 | 50 | 50 | n/a |
| SpecialTime 1 (minutes) | +2.5 | 60 | 60 | 60 | | n/a |
| SpecialTime 2 to shift CAUTION to ALARM (minutes) | | 960 | 960 | 960 | | n/a |
| GapTimeIndividual Maximum (minutes) | | 210 | 210 | 210 | | n/a |
| GapTime Window (minutes) | | 60 | 60 | 60 | | n/a |

TABLE 1c

| | Points | Standard Age 18 to 54 (predict) | Standard Age 55+ (predict) | Hi-Risk All Ages (predict) | ER (predict) | Apnea (detect) |
|---|---|---|---|---|---|---|
| Names of Parameters Used (defaults) | | | | | | |
| resolution | | 0.06 | 0.06 | 0.20 | 0.20 | 0.06 |
| outliers | | 3 | 3 | 3 | 3 | 3 |
| segment size | | 101 | 101 | 101 | 101 | 101 |
| Low-HRV | | | | | | |
| segments | +2.5 | 100 | 100 | 100 | 100 | n/a |
| maximum variation (seconds) | | 0.62 | 0.62 | 0.62 | 0.62 | n/a |
| segment exceptions | | 2 | 2 | 2 | 2 | n/a |
| ACRR | | | | | | |
| ALARMhigh | +2.5 | 50 | 65 | 30 | 50 | n/a |
| Cautionhigh | +2.5 | 50 | 65 | 30 | 50 | n/a |
| ALARMtime | | 35 | 52 | 135 | 40 | n/a |
| Cautiontime | | 35 | 52 | 135 | 40 | n/a |
| HEART RATE (bpm) | | | | | | |
| ALARMhigh | +2.5 | 135 | 135 | 120 | 135 | n/a |
| ALARMlow | +2.5 | 45 | 45 | 40 | 45 | n/a |
| CAUTIONhigh | +2.5 | 135 | 135 | 120 | 100 | n/a |
| CAUTIONlow | +2.5 | 45 | 45 | 40 | 45 | n/a |
| ALARMtime (minutes) | | 45 | 45 | 60 | 45 | n/a |
| Names of Formulas Used | | | | | | |
| Apnea detection | | | | | | |
| ALARMHIGH | | n/a | n/a | n/a | n/a | 3 |
| cautionhigh | | n/a | n/a | n/a | n/a | 3 |
| threshold | | n/a | n/a | n/a | n/a | 120 |
| outof | | n/a | n/a | n/a | n/a | 9 |

If at any time the points total +2.5 or higher, or −2.5 or lower, then the patient is at risk of experiencing a potentially fatal arrhythmia within the next two to 24 hours.

TABLES 1a, 1b and 1c set forth the following:

The settings predicting an adverse event for ambulatory patient's age 18 to 54;

the settings predicting an adverse event for ambulatory patients age 55 and older;

the settings predicting an adverse event for High Risk patients, e.g. patients of all ages in the Cardiac Care Unit (CCU);

the settings predicting an adverse event for patients of all ages in the Emergency Room (ER); and the settings for detecting a sleep apnea arousal.

In particular, the invention relates to the discovery that monitoring a variety of Kurtosis parameters for sympathetic and parasympathetic heart activity and then measuring these parameters against predetermined limits results in an accurate predictor of heart arrhythmia. Thus, part of the invention is that the inventor has determined key upper and lower values of ranges of these parameters for various classes of patients. Values within the ranges are normal. These parameters for a patient are measured and a score is calculated. When the score is sufficiently above or below normal, a caution signal or alarm signal is generated.

Knowing these predetermined values for a variety of parameters disclosed by this specification enables one skilled in the art to select other Kurtosis parameters of low variability or high variability activity and determine high and low values of these parameters which define normal ranges and values which predict arrhythmia. Measurement of more than one parameter leads to more accurate predictions.

In TABLES 1a, 1b and 1c, the first columns under "(defaults)" list resolution which is the number of 0.02 Time Intervals whose values are averaged together. These first columns also list outliers, which are the three longest Time Intervals and the 3 shortest Time Intervals in a Time Segment, which are deleted before any formula calculations are made. These first columns also list segment size, which is the number of NN Time Intervals in a Time Segment after ACRRs are removed and stored separately, and MARRs (FIG. 9d) are removed and stored separately, and outliers are deleted.

Post-MI (myocardial infarction) patients will use one of the two Standard settings, depending on age. If, in a 24 hour period ALARMS are triggered and the patient experiences an adverse cardiac event, then the Hi-Risk settings are substituted for a 24 hour period. If the patient still triggers ALARMS and the patient does not experience an adverse cardiac event, then the software would have to be customized for that patient.

These first columns also list the titles to the group of absolute formulas ABS.SPS; ABS.AMo; ABS.DX; ABS.DX/M; low-HRV; ACRR; Heart Rate; and NN-Acceleration relating to the SPS formulas.

The term "ABS" is an abbreviation for "absolute." Thus, these values are applied to all patients in the specified category. For example, ABS.SPS is an absolute value (upper or lower limit) of SPS (sympathetic/parasympathetic stress).

The patient's measured value of SPS is compared to the ABS.SPS limits to determine if the patient's health is in danger.

TABLE 1a discloses the parameters relating to upper and lower limits for SPS as well as upper and lower limits for AMo.

TABLE 1b discloses the parameters relating to the upper and lower limits of DX as well as the upper and lower limits of DX/M. TABLE 1b also provides for Special Time and Gap Time parameters.

TABLE 1c discloses low-HRV (defined above); ACRR (defined above); heart rate; and NN-Acceleration.

For example, for patients age 18 to 54, if a patient records 30 or more Time Segments out of 50 Time Segments where the patient's SPS value is 48 or higher, or 25 or more Time Segments out of 50 Time Segments where the patient's SPS value is 2.50 or lower, then the patient is experiencing an SPS ALARM condition, which is assigned a value +1.0 points if the formula value is 48 or larger, and a value of −1.0 points if the value is 2.50, or less.

If the patient records 5 to 29 Time Segments out of 50 Time Segments, where the patient's SPS value is 48 or higher, then the patient is experiencing a Caution condition, which is assigned a value of +0.5 points. If a patient records 15 to 24 Time Segments out of 50 Time Segments, where the patient's SPS value is an SPS value of 2.50 or lower, then patient is experiencing an SPS Caution condition, which is assigned a value of −0.5 points.

The same analysis set forth above, applies to patients in the other categories of TABLES 1a–c.

FIGS. 2a through 2g are charts, which deal with a patient's cardiac condition. The total points, if any, are totaled in the top chart, FIG. 2h, HRV Status. Points are assigned to each cardiac condition as set forth in TABLES 1a, 1b and 1c.

In FIGS. 2a through 2d, a Caution condition is assigned a value of either +0.5 if decreased variability is indicated, or −0.5 if increased variability is indicated. An ALARM condition is assigned a value of either +1.0 if decreased variability is indicated, or −1.0 if increased variability is indicated.

In FIG. 2e an ACRR ALARM condition (there is no Caution) is assigned a value of either +2.5 or −2.5, depending upon the cardiac condition indicated in FIGS. 2a through 2d, which is either decreased variability and thus an ALARM of +2.5, or increased variability, and thus an ALARM of −2.5. If neither a decreased nor an increased variability is indicated in FIGS. 2a through 2d, then the ALARM is +2.5, with no more than two consecutive time intervals which did not qualify as an ACRR Time Interval.

In FIG. 2f a low HRV ALARM condition (there is no Caution) is assigned a value of +2.5.

In FIG. 2g a Heart Rate ALARM condition, (there is no Caution) is assigned a value of either +2.5 or −2.5, depending upon the cardiac condition indicated in FIGS. 2a through 2d, which is either decreased variability and thus an ALARM of +2.5, or increased variability, and thus an ALARM of −2.5. If neither a decreased nor an increased variability is indicated in FIGS. 2a through 2d, then the ALARM is +2.5.

In FIG. 2h, numeral 141 indicates the +2.5 HRV Status ALARM level of decreased variability. Numeral 143 indicates +2.0 HRV Status Caution level of decreased variability. Numeral 145 indicates zero, 0, HRV Status level. Numeral 147 indicates −2.0 HRV Status Caution level of increased variability. Numeral 149 indicates −2.5 HRV Status ALARM level of increased variability. Numeral 151 indicates the sum of all the Cautions and/or ALARMS as may be recorded in FIGS. 2a through 2g.

Figure 2A:
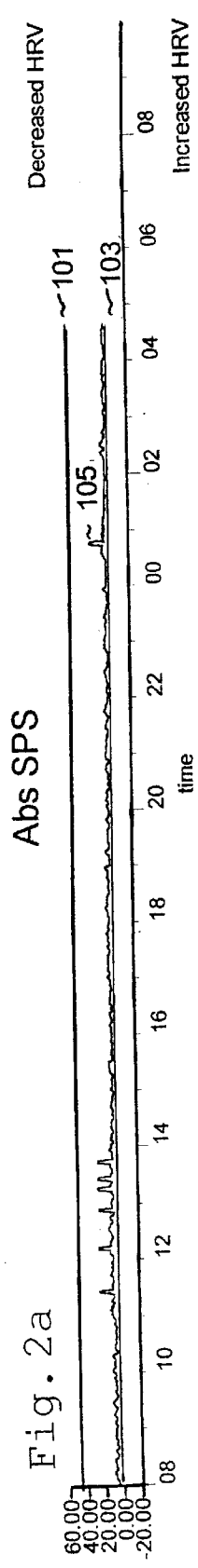
FIG. 2a shows a plot of Abs SPS versus time.

In FIG. 2a, numeral 101 indicates the decreased variability ALARM level for the formula Abs SPS. Numeral 103 indicates the increased variability ALARM level for the formula Abs SPS. Numeral 105 indicates the patient's recorded value for the Abs SPS formula.

Figure 2B:
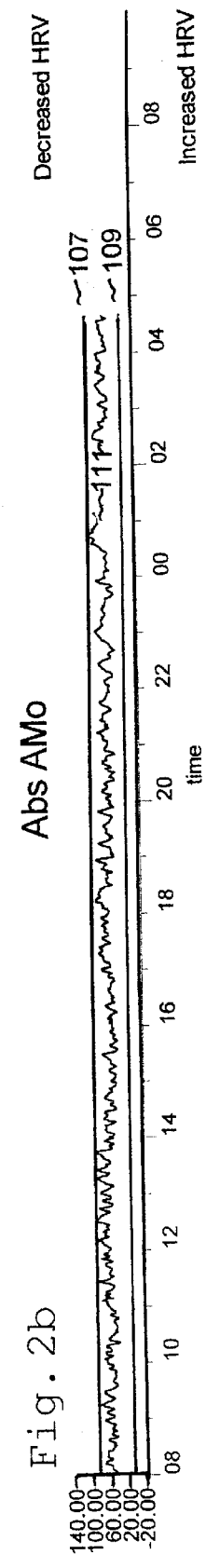
FIG. 2b shows a plot of Abs AMo versus time.

In FIG. 2b, numeral 107 indicates the decreased variability ALARM level for the formulas Abs AMo. Numeral 109 indicates the increased variability ALARM level for the formula Abs AMo. Numeral 111 indicates the patient's recorded value for the Abs AMo formula.

Figure 2C:
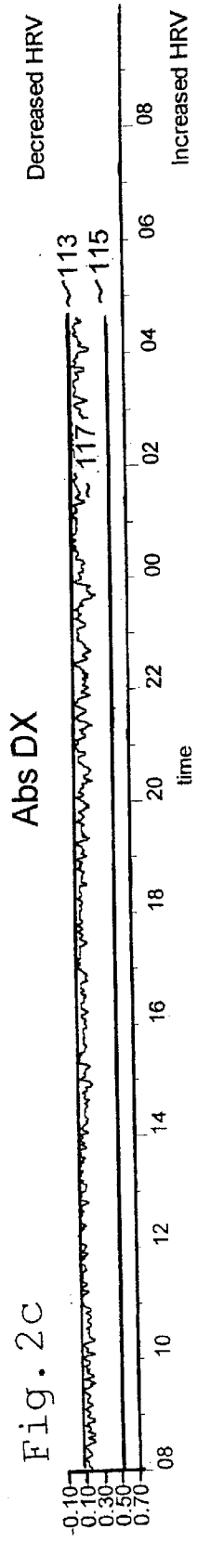
FIG. 2c shows a plot of Abs DX versus time.

In FIG. 2c, numeral 113 indicates the decreased variability ALARM level for the formula Abs DX. Numeral 115 indicates the increased variability ALARM level for the formula Abs DX. numeral 117 indicates the patient's recorded value for the Abs DX formula.

In FIG. 2d, numeral 119 indicates the decreased variability ALARM level for the formula Abs DX/Median. Numeral 121 indicates the increased variability ALARM level for the formula DX/Median. Numeral 123 indicates the patient's recorded value for the DX/Median formula.

In FIG. 2e, numeral 129 indicates the ALARM level for Low HRV. Numeral 131 indicates the patient's recorded level for Low HRV.

In FIG. 2f, numeral 125 indicates the upper ALARM limit of ACRRs per 101 NN heart beats. Numeral 127 indicates the patient's recorded value for ACRRs.

In FIG. 2g, numeral 133 indicates the upper ALARM level for Heart Rate. Numeral 137 indicates the lower ALARM level for Heart rate. Numeral 135 indicates the difference between numeral 133 and numeral 137. 139 indicates the patient's recorded level for Heart Rate.

FIGS. 3a through 3g are charts, which deal with a patient's cardiac condition. The total points, if any, are totaled in the top chart, FIG. 3h, HRV Status. Points are assigned to each cardiac condition as set forth in TABLES 1a, 1b and 1c.

In FIGS. 3a through 3e, numeral 150 indicates both decreased and increased heart rate variability Cautions, and numeral 152 , ALARMS.

In FIG. 3f, numeral 152 indicates both decreased and increased heart rate variability ALARMS.

FIG. 3g indicates heart rate.

Figure 3H:
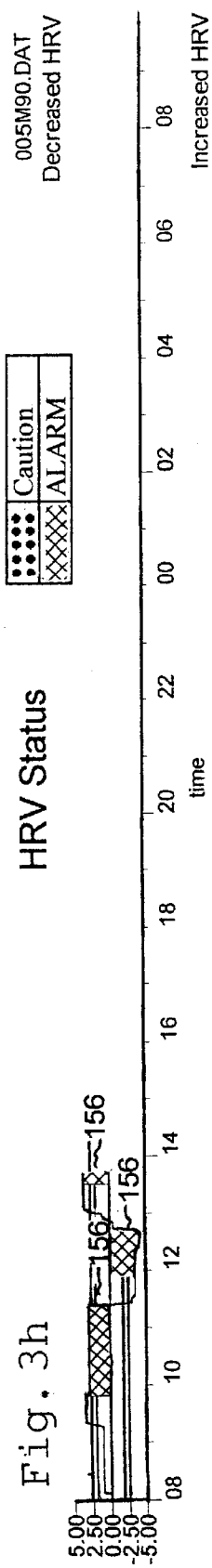
FIG. 3h shows a plot of HRV Status versus time.
Figure 3A:
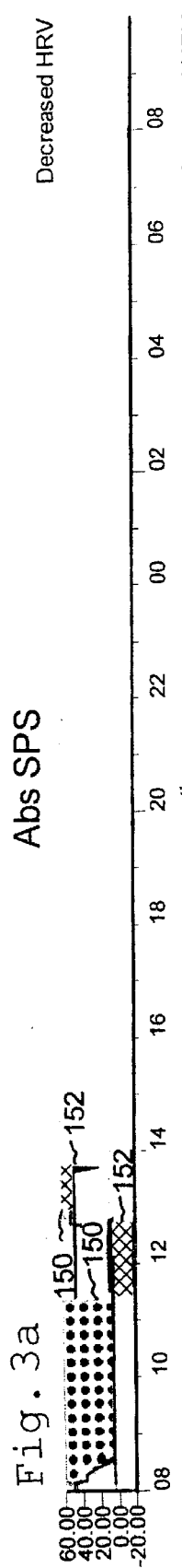
FIG. 3a shows a plot of Abs SPS versus time.
Figure 3B:
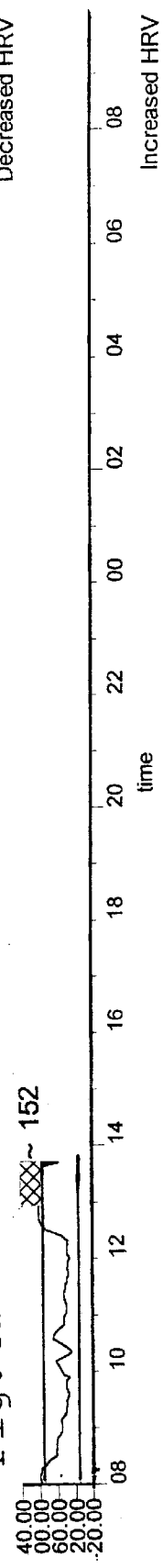
FIG. 3b shows a plot of Abs AMo versus time.
Figure 3C:
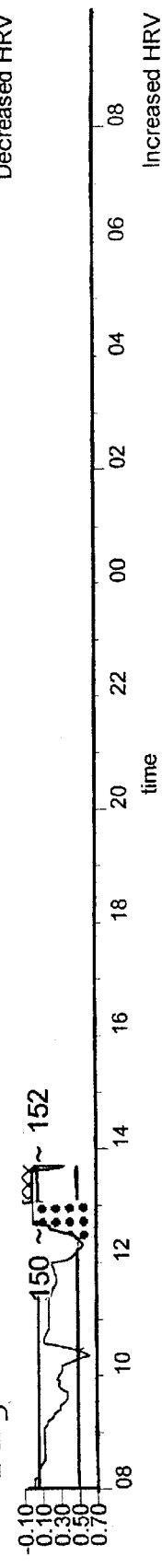
FIG. 3c shows a plot of Abs DX versus time.

In FIG. 3h, numeral 156 indicates first a decreased heart variability ALARM, then an increased heart variability ALARM, and then finally a decreased heart variability ALARM.

FIGS. 4a through 4g are charts, which deal with a patient's cardiac condition. The total points, if any, are totaled in the top chart, FIG. 4h, HRV Status. Points are assigned to each cardiac condition as set forth in TABLES 1a, 1b and 1c.

In FIGS. 4a through 4e numeral 152 (if present) indicates increased heart rate variability ALARMS.

In FIG. 4f, numeral 152 indicates both decreased and increased heart rate variability ALARMS.

FIG. 4g indicates heart rate.

In FIG. 4h, numeral 154 indicates an increased variability HRV Status Caution, and numeral 156 indicates an increased variability HRV Status ALARM.

FIGS. 5a through 5g are charts, which deal with patient's cardiac condition. The total points, if any, are totaled in the top chart, FIG. 5h, HRV Status. Points are assigned to each cardiac condition as set forth in TABLES 1a, 1b and 1c.

Figure 5D:
FIG. 5d shows a plot of DX/Median versus time.
Figure 5E:
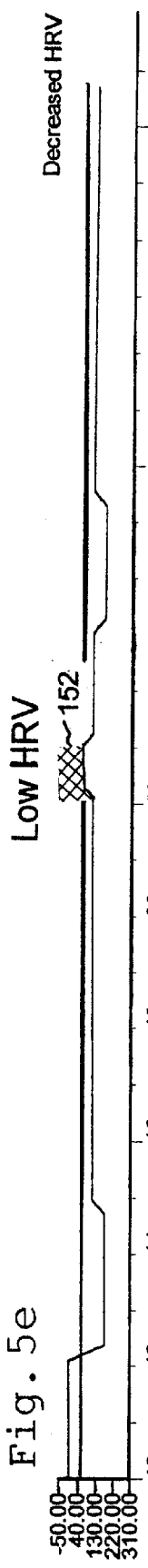
FIG. 5e shows a plot of Low HRV versus time.
Figure 5F:
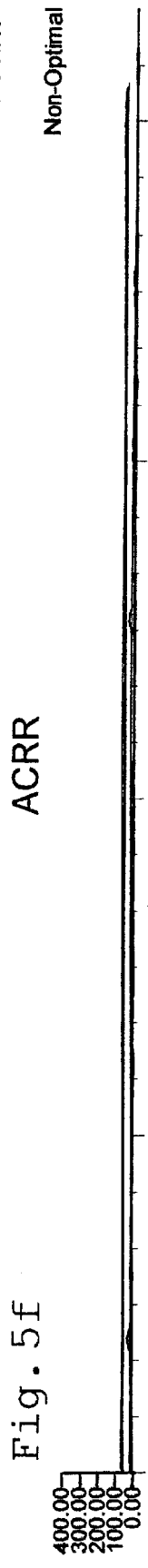
FIG. 5f shows a plot of ACRR versus time.
Figure 5G:
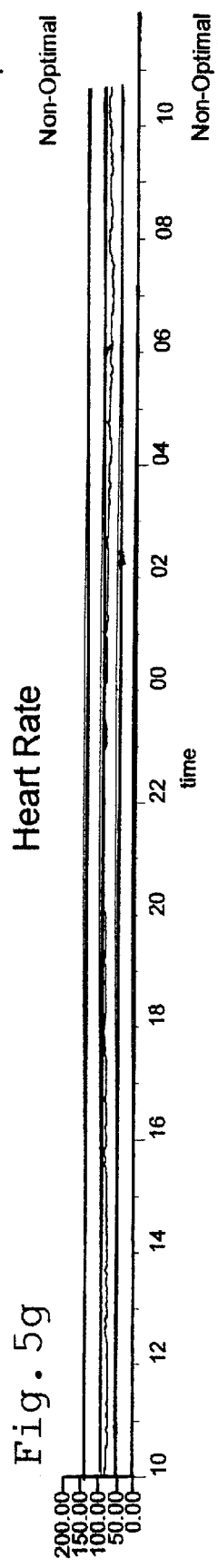
FIG. 5g shows a plot of Heart Rate versus time.
Figure 6C:
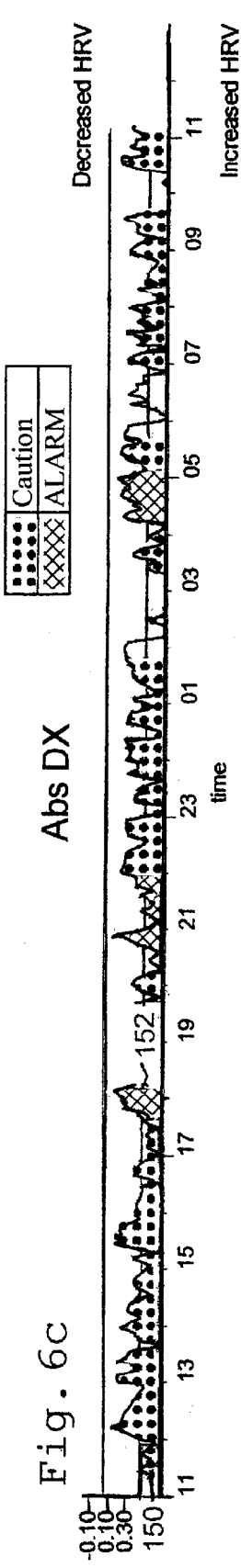
FIG. 6c shows a plot of Abs DX versus time.
Figure 6E:
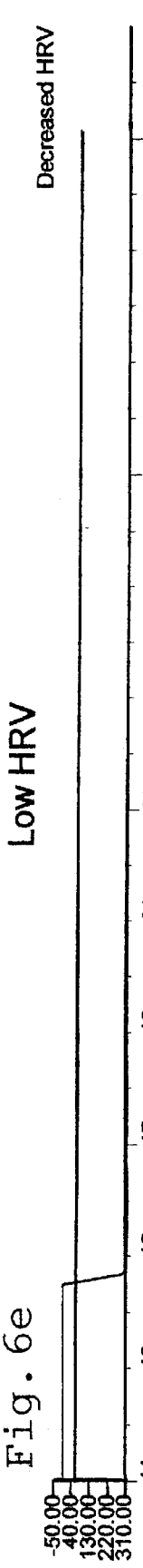
FIG. 6e shows a plot of Low HRV versus time.
Figure 6F:
FIG. 6f shows a plot of ACRR versus time.
Figure 6G:
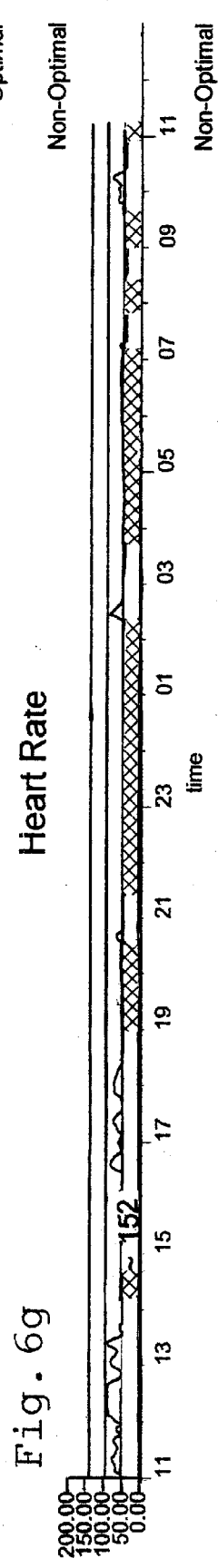
FIG. 6g shows a plot of Heart Rate versus time.
Figures 7A, 7B, 7C:
FIGS. 7a, 7b, and 7c show people carrying a cellular telephone, which would be silently activated to Dial 911, or a central monitoring station when an ALARM condition was predicted by the wrist monitor concealed under their sleeves.
Figure 8:
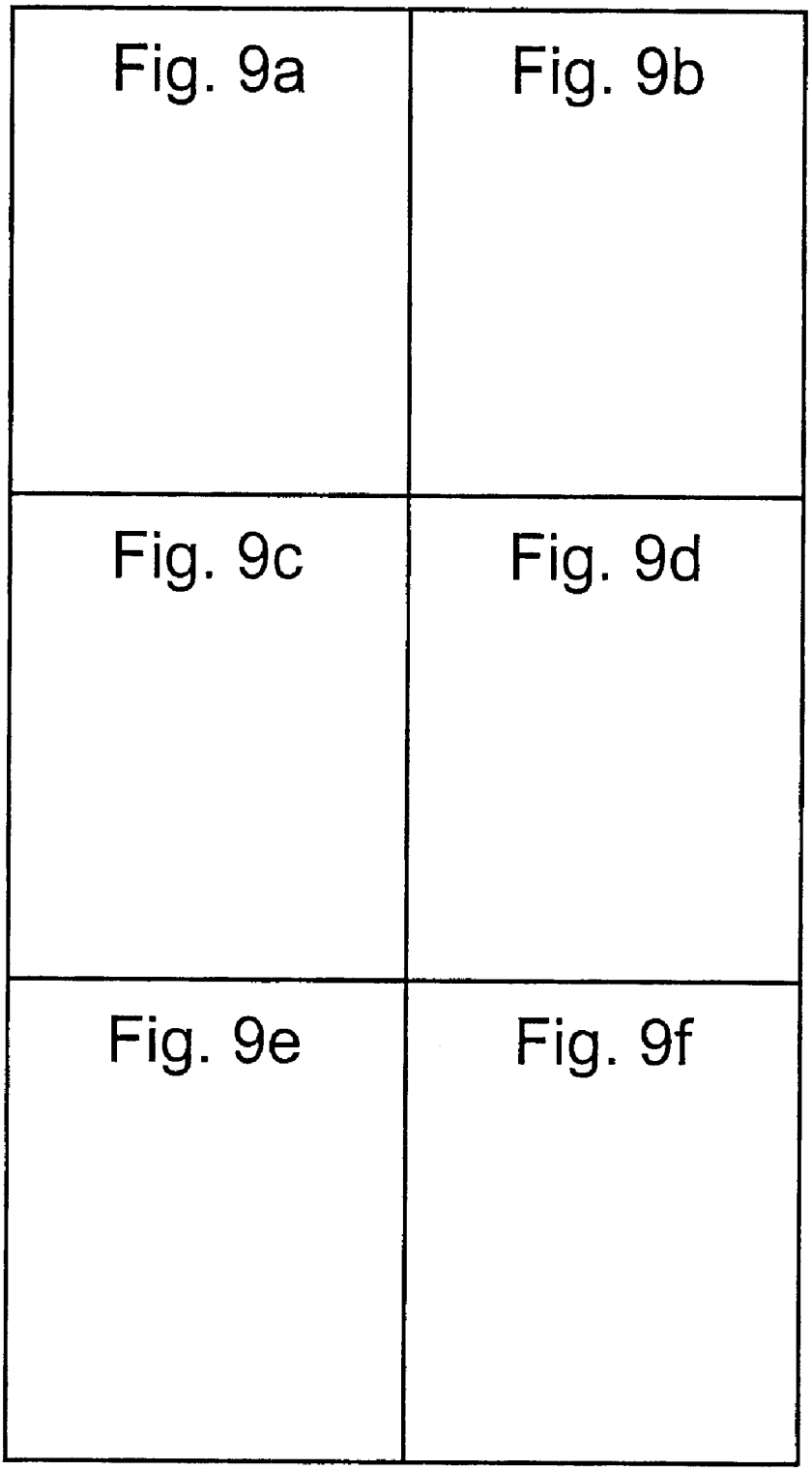
FIG. 8 schematically shows an overall view of a process decision tree diagram of an embodiment of the present invention.

In FIG. 5e, numeral 152 indicates a decreased variability Low HRV ALARM.

In FIG. 5h, numeral 156 indicates a decreased variability HRV Status ALARM.

FIGS. 6a through 6g are charts, which deal with patient's cardiac condition. The total points, if any, are totaled in the top chart, FIG. 6h, HRV Status. Points are assigned to each cardiac condition as set forth in TABLES 1a, 1b and 1c.

In FIGS. 6a through 6g, several high variability CAUTIONS, numeral 150, and ALARMS, numeral 152 are indicated.

Parameter Ranges

The parameter upper and lower limits listed in the Tables 1a–c may be employed over a range of typically less than about ±10%, preferably less than about ±5%.

For example: For SPS (Sympathetic Parasympathetic Stress), for ambulatory patients age 18 to 54, the upper limit listed on Table 1a is 48 for at least 30 out of 50 Time Segments. However, in practice an upper limit is selected in the range from 46 to 50 for at least 30 out of 50 Time Segments.

In general, the CAUTION or ALARM signal for the particular parameter may operate suitably if the number of trigger segments (listed in the Tables 1a–c for that respective parameter) are adjusted by ±2, preferably ±1, so long as the adjustment is at most 20% of the number of trigger segments (listed in the Tables 1a–c for that respective parameter) rounded off to the nearest integer.

For example, for SPS (Sympathetic Parasympathetic Stress), for ambulatory patients age 18 to 54, Table 1a lists an ABS.SPS.HI Caution signal when the value for SPS is greater than or equal to the upper limit of 48 for a ratio of at least 5 of 50 Time Segments. A suitable range for "about 5" is 4 to 6 out of 50 Time Segments. Table 1a lists an ABS.SPS.HI ALARM signal when the value for SPS is greater than or equal to the upper limit of 48 for a ratio of at least about 30 out of 50 Time Segments. A practical range for a ratio of "about 30" is 28 to 32 out of 50 Time Segments.

Moreover, the number of CAUTION segments and/or ALARM segments of 101 Time Intervals can be reduced by as much as 40%, preferably by as much as 20% and still be used to predict heart conditions, so long as the ratios of trigger segments to Caution segments and ALARM segments, of Tables 1a, 1b, and 1c with at most the above-described adjustments, are employed. Thus, in obtaining these ratios, at least 30, preferably at least about 50 Time Segments are measured.

For example, for ABS.SPS.HI ALARM of a standard ambulatory person age 18 to 54, Table 1a lists 30 out of 50 Time Segments to signal an alarm. However, 24 out of 30 Time Segments could also signal an alarm because this maintains the ratio listed by Table 1a.

Thus, ranges for other parameters of the present invention for a standard ambulatory person age 18 to 54 are described as follows.

For the SPS lower limit, for ambulatory patients age 18 to 54, of about 2.5, a CAUTION is signaled when the value for SPS is less than or equal to the lower limit for a ratio of at least about 13 to 17 out of 50 Time Segments, and an ALARM is signaled when the value for SPS is less than or equal to the lower limit for a ratio of at least about 23–27 out of 50 Time Segments. In obtaining these ratios, at least about 30, preferably at least about 50, Time Segments are measured.

For AMo (Amplitude of the Mode) for ambulatory patients age 18 to 54, the upper limit is about 85 to about 95 and a CAUTION is signaled when the value for AMo is greater than or equal to the upper limit for a ratio of at least about 13 to 17 out of 50 Time Segments, and an ALARM is signaled when the value for AMo is greater than or equal to the upper limit for a ratio of at least about 28 to 32 out of 50 Time Segments, wherein at least about 30, preferably at least about 50, Time Segments are measured.

Also, for AMo for ambulatory patients age 18 to 54, the lower limit is about 8 to about 12, and a Caution is signaled when the value for AMo is less than or equal to the lower limit for a ratio of at least about 13 to 17 out of 50 Time Segments, and an ALARM is signaled when the value for AMo is less than or equal to the lower limit for a ratio of at least about 23 to 27 out of 50 Time Segments, wherein at least about 30, preferably at least about 50 Time Segments are measured.

For DX (Delta X) for ambulatory patients age 18 to 54, the upper limit is about 0.4 to about 0.6 and a Caution is signaled when the value for DX is greater than or equal to the upper limit for a ratio of at least about 13 to about 17 out of 50 Time Segments, and an ALARM is signaled when the value for DX is greater than or equal to the upper limit for a ratio of at least about 28 to 32 out of 50 Time Segments, wherein at least about 30, preferably at least about 50 Time Segments are measured.

Also, for DX (Delta X) for ambulatory patients age 18 to 54, the lower limit is about 0.05 to about 0.07 and a Caution is signaled when the value for DX is less than or equal to the lower limit for a ratio of at least about 8 to about 12 out of 50 Time Segments, and an ALARM is signaled when the value for DX is less than or equal to the lower limit for a ratio of at least about 23 to about 27 out of 50 Time Segments, wherein at least about 30, preferably at least about 50 Time Segments are measured.

For DX/M for ambulatory patients age 18 to 54, the upper limit is about 0.4 to 0.5 and a Caution is signaled when the value for DX/M is greater than or equal to the upper limit for a ratio of at least about 13 to about 17 out of 50 Time Segments, and an ALARM is signaled when the value for DX/M is greater than or equal to the upper limit for a ratio of at least about 23 to about 27 out of 50 Time Segments, wherein at least about 30, preferably at least about 50, Time Segments are measured.

Also, for DX/M for ambulatory patients age 18 to 54, the lower limit Caution is about 0.015 to about 0.025, a Caution is signaled when the value for DX/M is less than or equal to the lower limit for a ratio of at least about 4 to 6 out of 50 Time Segments, and an ALARM is signaled when the value for DX/M is less than or equal to the lower limit for a ratio of at least about 23 to 27 out of 50 Time Segments, wherein at least about 30, preferably at least about 50, Time Segments are measured.

For Low-HR, Table 1c lists a maximum variation of 0.62 seconds or lower for 100 or more Time Segments with no more than 2 exceptions. The maximum variation may be selected from a range of about 0.56 to about 0.68 seconds.

Table 1c lists ACRRs, for a standard 18 to 54 year old person, as when the present Time Interval differs from the previous Time Interval by about +25% or about −25%, and this situation occurs for a ratio of about 50 or more times while accumulating a Time Segment of 101 NN Time Intervals. If this condition persists for 35 minutes, or longer, then this is either a +2.5 or −2.5 point ALARM. It is suitable to select a time from 30 to 40 minutes to signal an ALARM.

Pacemaker and Cardiodefibrillator with a Pacemaker

At present, pacing is accomplished by making all beats the same duration in time. TABLE 2 is a pacing schedule that can be incorporated in an implantable cardioverter defibrillator, which induces much more natural pacing. Also, TABLE 2 shows the typical longest and shortest values of Time Intervals in a Time Segment and subtracts the two numbers to calculate DX.

TABLE 2

| Breaths/ Minute | | Heart Rate (sec) | beats per min. (bpm) | AMo | AMo Secs | (Longest minus shortest) DX |
|---|---|---|---|---|---|---|
| 24 > 27+ | | 0.44 | | | | (0.50 – 0.42) |
| | Mode | 0.46 | 130 | 50 | 0.46 | |
| | | 0.48 | | | | DX = 0.08 |
| 22 > 25+ | | 0.50 | | | | (0.56 – 0.46) |
| | Mode | 0.52 | 115 | 47 | 0.52 | |
| | | 0.54 | | | | DX = 0.10 |
| 20 > 23 | | 0.56 | | | | (0.64 – 0.52) |
| | Mode | 0.58 | 103 | 44 | 0.58 | |
| | | 0.60 | | | | DX = 0.12 |
| 18 > 21 | | 0.62 | | | | (0.70 – 0.56) |
| | Mode | 0.64 | 94 | 41 | 0.64 | |
| | | 0.66 | | | | DX = 0.14 |
| 16 > 19 | | 0.68 | | | | (0.76 – 0.60) |
| | Mode | 0.70 | 86 | 38 | 0.70 | |
| | | 0.72 | | | | DX = 0.16 |
| 14 > 17 | | 0.74 | | | | (0.82 – 0.64) |
| | Mode | 0.76 | 79 | 35 | 0.76 | |
| | | 0.78 | | | | DX = 0.18 |
| 12 > 15 | | 0.80 | | | | (0.88 – 0.68) |
| | Mode | 0.82 | 73 | 32 | 0.82 | |
| | | 0.84 | | | | DX = 0.20 |
| 10 > 13 | | 0.86 | | | | (0.96 – 0.74) |
| | Mode | 0.88 | 68 | 29 | 0.88 | |
| | | 0.90 | | | | DX = 0.22 |
| 8 > 11 | | 0.92 | | | | (1.04 – 0.80) |
| | Mode | 0.94 | 64 | 26 | 0.94 | |
| | | 0.96 | | | | DX = 0.24 |
| 5 > 9 | | 0.98 | | | | (1.12 – 0.86) |
| | Mode | 1.00 | 60 | 23 | 1.00 | |
| | | 1.02 | | | | DX = 0.26 |

In TABLE 2, ranges such as 5>9 mean 5 to 9. Mode means the heart rate and 24>27+ is breaths per minute. The number of heart beats in a Time Segment typically ranges from about 25 to about 300, preferably ranges from about 50 to about 200, and most preferably is about 101.

TABLE 2 shows a breaths per minute column. For example, if the patient's breathing cycle is detected to be in the range of 14 to 17 breaths per minutes, the pacing range would range from 0.82 seconds to 0.64 seconds, as set forth in column DX, for 101 beats. The most frequently occurring beat for this patient would be 0.76 seconds, which would occur 35 times out of 101 beats. Thus, the AMo is 35. Of course the same ratios may be applied over Time Segments having more or less than 101 Time Intervals, e.g., from about 25 to about 300 Time Intervals.

The breaths per minute associated with a shown group of values for the parameters of heart rate and bpm, AMo, AMo Secs and DX can be shifted up or down to account for age or to overdrive the patient's heart when required. For example, TABLE 3 shows 24>27 breaths per minute associated with the following parameter values: Heart rate at mode 0.46 sec, 130 bpm, AMo=50, AMo Secs 0.46, and DX=0.08. If desired, 24–27 breaths per minute may be shifted to be associated with the parameter values which TABLE 3 shows associated with 22–25 breaths/minute, namely, Heart Rate at mode 0.52, 115 bpm, AMo=47, AMo Secs=0.52 and DX=0.10.

As an alternative to the natural pacing described above, software for the parameters described in FIGS. 1a–b and Tables 1a, 1b and 1c may be employed. If the software triggers an ALARM condition, then it triggers a vagal nerve stimulator incorporated with the implantable cardioverter defibrillator to stimulate the vagal in the expectation that the ALARM conditions predicted by the software would cease.

Wrist Monitor Decision Tree

The explanation of the wrist monitor decision tree, is contained in FIGS. 8 and 9a–f in which steps are identified by reference numbers. FIG. 10 shows an apparatus of the present invention which includes a wrist monitor 1921. The patient obtains the wrist monitor, step 901 (FIG. 9b), the wrist monitor 1921 (FIG. 9a) is either connected to the patient's wrist, step 902 (FIG. 9b), or it is not connected step 928, as determined by a galvanic skin sensor attached to the wrist monitor's band. When the wrist monitor 1921 is connected to the patient's wrist, step 902, the date and time is recorded in the memory of the wrist monitor 1921, step 901a. Should the patient remove the wrist monitor 1921 from his/her wrist, then the date and time is recorded in the memory of the wrist monitor 1921, step 901a.

After the connection of the wrist monitor, 1921 to the patient's wrist, step 902, then either a pulse wave is detected, step 906, or no pulse wave is detected, step 908. If no pulse wave is detected, step 908, then a prerecorded message will sound from the wrist monitor, step 921 instructing the patient to try repositioning the pulse sensor over the radial artery. If after, say five minutes no pulse is detected, then a pre-recorded message will instruct the patient to substitute a two electrode ECG waist band for the pulse sensor.

Finally, the wrist monitor 1921 will detect movement in the patient's arm, step 910, or it will not detect motion, step 920, using a strain gauge or some other piezo electric device.

Figure 9A:
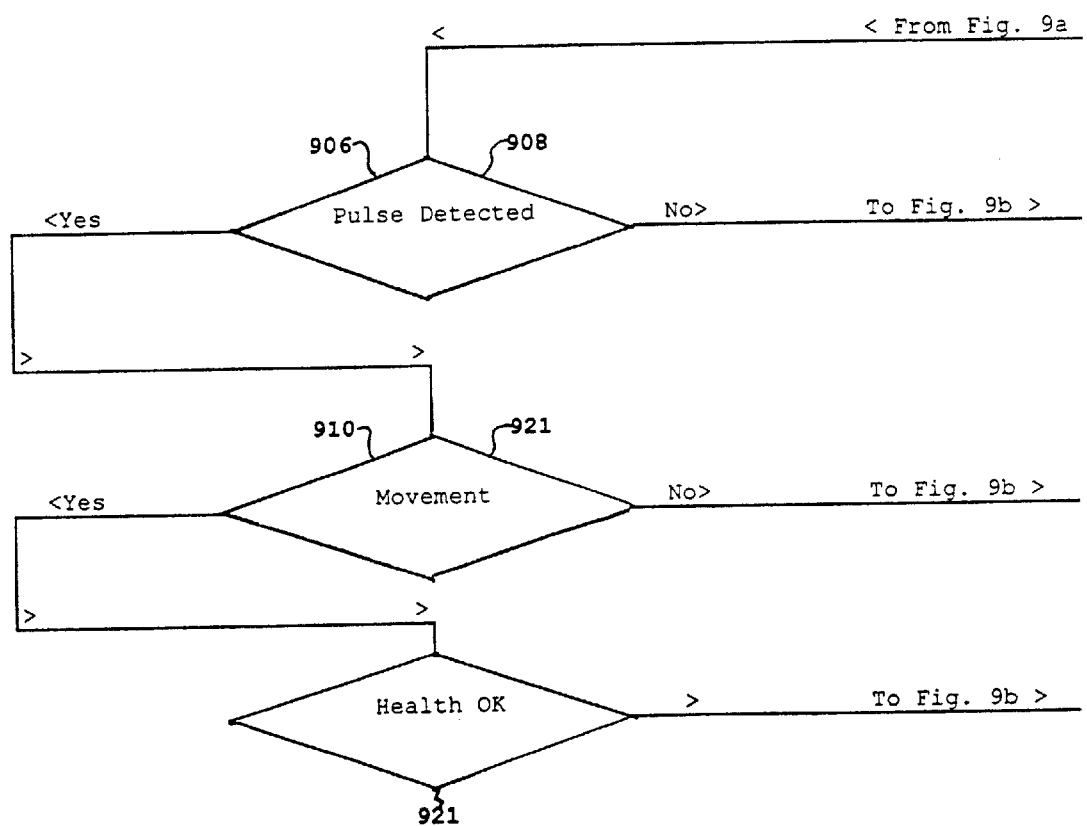
Figure 9B:
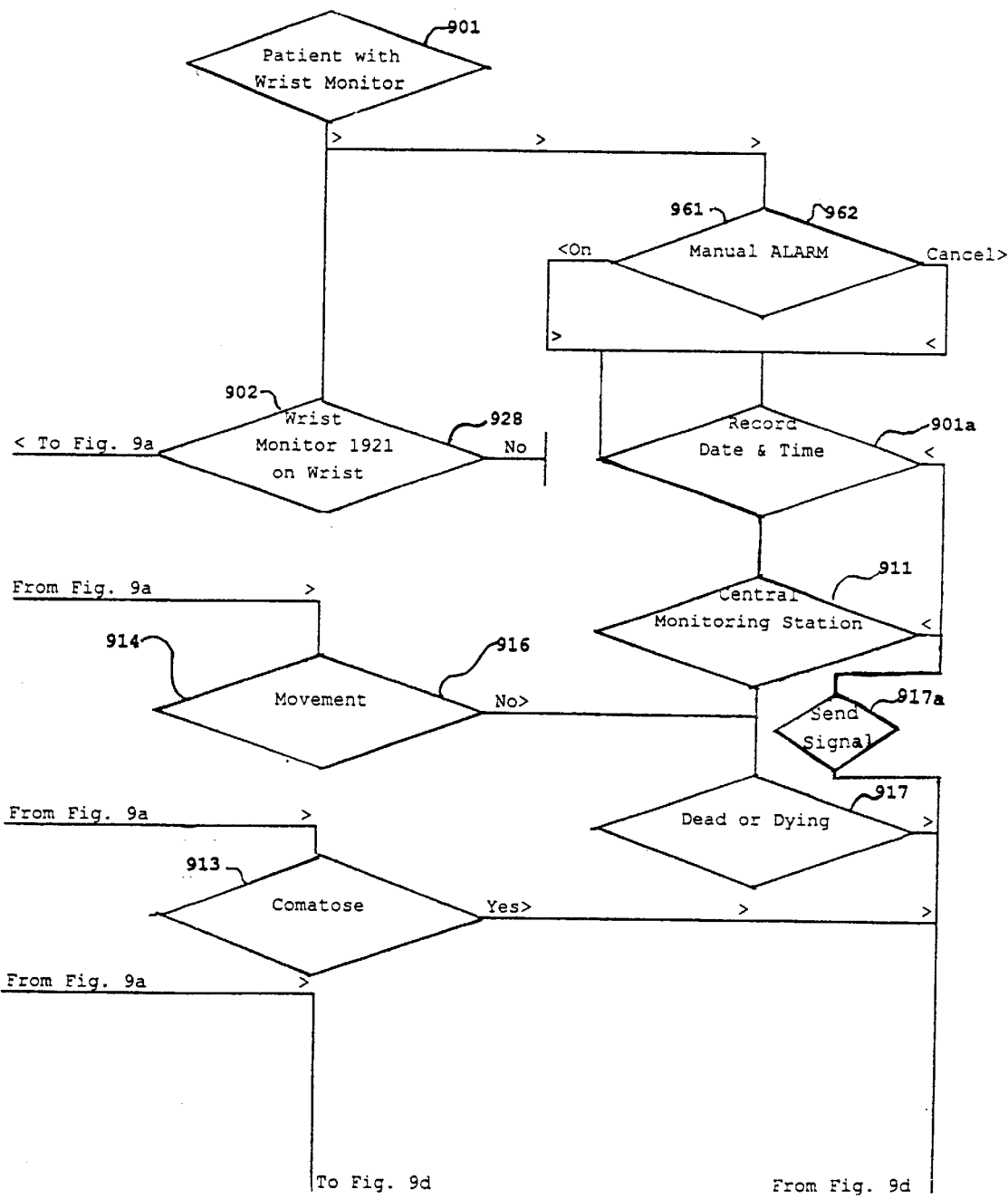
Figure 10:
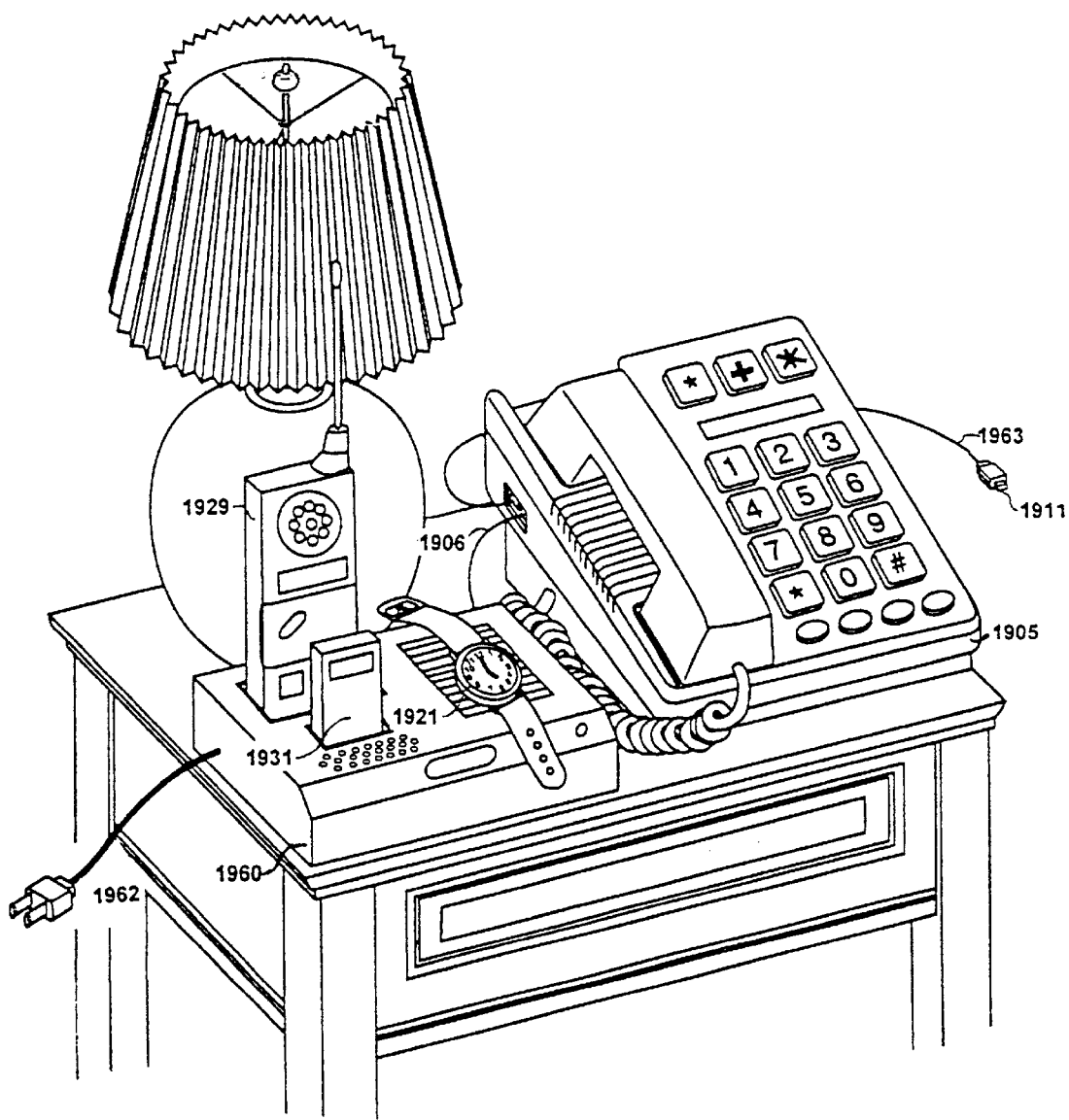
FIG. 10, shows a Recharge Base Station.

If the wrist monitor 1921, is connected, step 902, and detects a pulse, step 906, and detects movement, step 910, and no HRV Status ALARMS, nor high ACRR ALARMS, nor MARR ALARMs, then the patient's health is acceptable, step 918 (FIG. 9a).

If the wrist monitor 1921 is connected, step 902 (FIG. 9b), and detects a pulse, step 906, but does not detect movements, step 921 (FIG. 9a), then it is assumed the patient is comatose, step 913 (FIG. 9b), and a signal is sent, step 917a, to the patient's land line 1905, or cellular telephone 1929, to dial a central monitoring station, step 911 (FIG. 9b), the central monitoring station will call the local Emergency Medical Service (EMS), which is equipped with caller ID, and thus knows the patient's location to which they will dispatch an ambulance and transport the patient to the Emergency Room.

If the wrist monitor 1921, is connected, step 902, and does not detect a pulse, step 908, and does not detect movement, step 916, then it is assumed the patient is dying or dead, step 917, and a signal is sent to the patient's land line 1905, or cellular telephone 1929 to dial the Central monitoring station 911 (FIG. 9b) or the local Emergency Medical Service (EMS), which is equipped with caller ID and thus knows the patient's location to which EMS will dispatch an ambulance and transport the patient to the Emergency Room.

Should a patient experience an ALARM condition and wish to report it to the central monitoring station 911, then the patient can report the ALARM condition to the central monitoring station 911, by pushing a button on his/her wrist monitor 1921, step 961 (FIG. 9b), and the date and time is recorded in the memory of the wrist monitor 1921, step 901a. Should a patient want to cancel an ALARM condition reported to the central monitoring station, step 911, then the patient can cancel the ALARM condition to the central monitoring station, step 911, by pushing a different button on his/her wrist monitor 1921, step 962 (FIG. 9b), and the date and time is recorded in the memory of the wrist monitor 1921, step 901a.

If the wrist monitor 1921 (FIG. 10) detects movement just prior to a pulse wave, step 910 (FIG. 9a), then that pulse wave RR is designated a MARR, Motion artifact RR, step 923 (FIG. 9d), and is stored in a separate bin. A bin is a term of computer art for a separate storage area. Should more than four minutes of continuous MARRs be accumulated, then the wrist monitor 1921 automatically calls the central monitoring station 911 (FIG. 9b), and apprizes them of the patient's excessive MARR's condition. The central monitoring station 911, then calls the patient, step 911 (FIG. 9e), to try and determine the cause of the MARRs, and suggest to the patient the appropriate action.

Figure 9D:
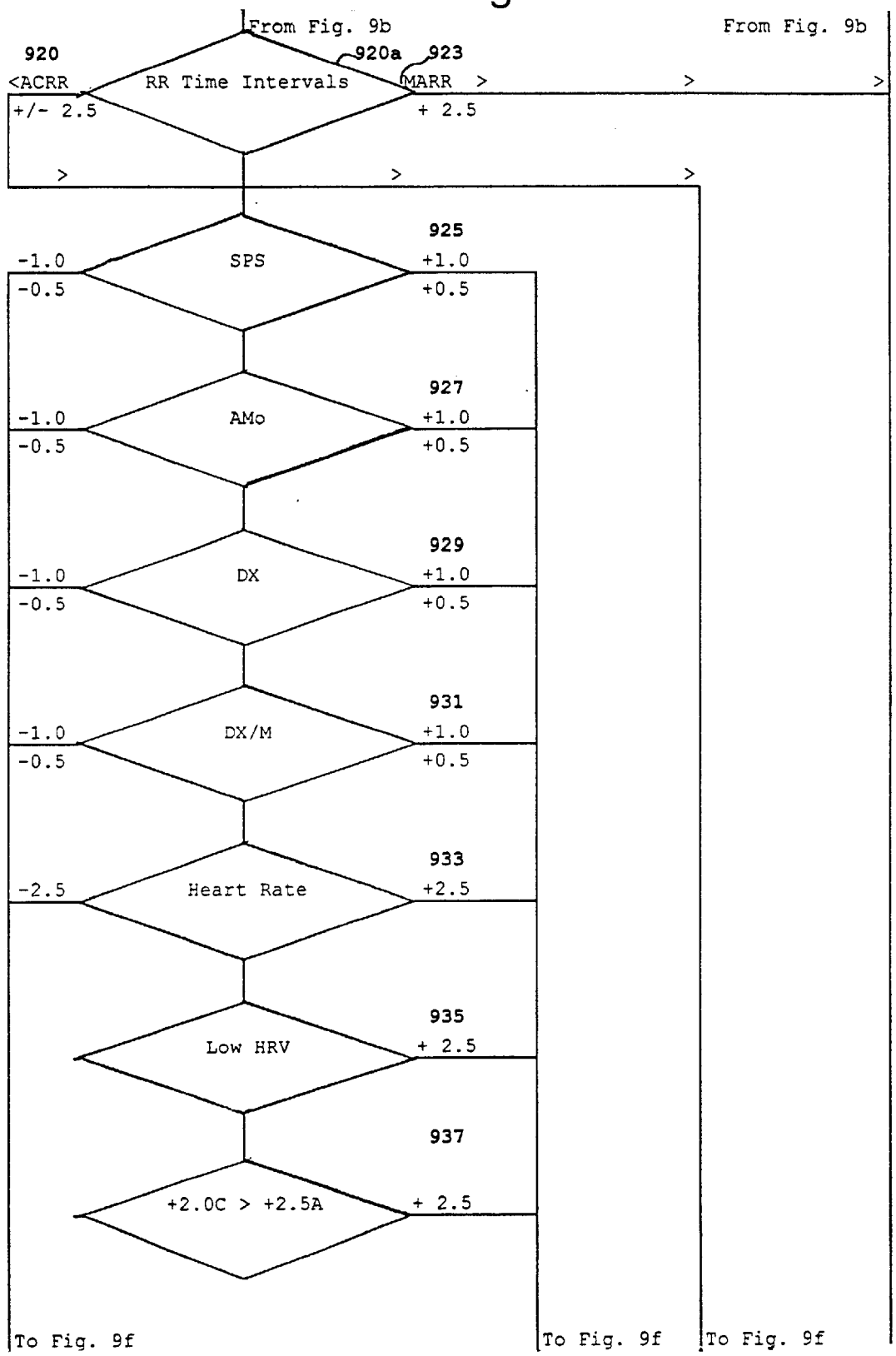
Figure 9E:
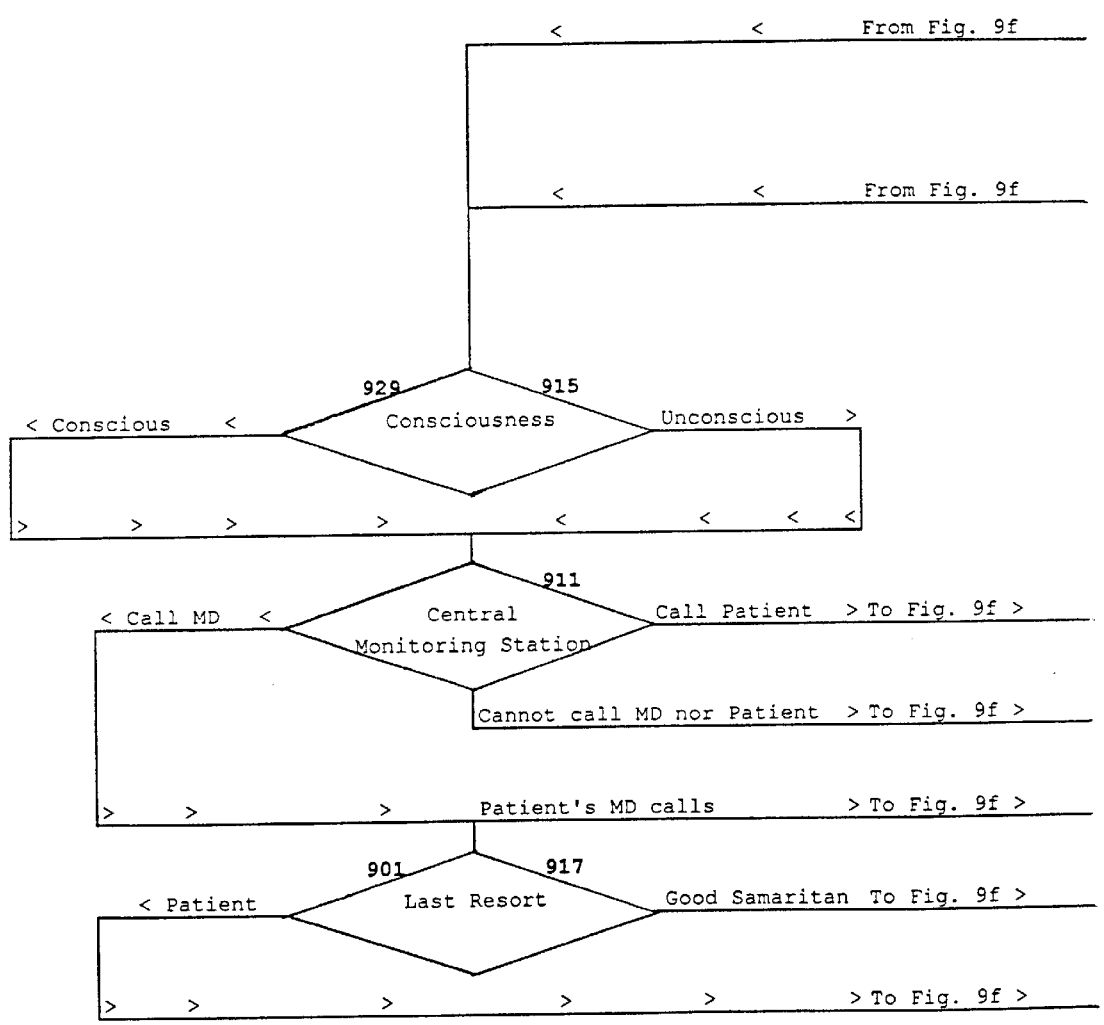

If the patient is home, and the patient's land line does not have a dial tone, then the ALARM message is transmitted, by the patient's cellular telephone 1929, step 941 (FIG. 9f) and pager 1931, step 945, to the central monitoring station, step 911 (FIG. 9e). As a last resort, either the patient, step 901, or a Good Samaritan, step 917, may rescue the patient (FIG. 9e).

Also, after movement is detected, then the sympathetic and parasympathetic parameters are measured (FIG. 9d). In operation, the wrist monitor 1921 separately stores ACRRs, step 920, and MARRs, step 923, and deletes the outliners, such that 101 NN Time Intervals remain which constitutes a Time Segment. Of course a Time Segment can be made with a different number of NN or RR Time Intervals as explained elsewhere in this specification. If an ALARM condition is detected, step 939 (FIG. 9f), the central monitoring station is contacted, step 911 (FIG. 9e) via a land line, step 943, cell phone, step 941, and/or pager, step 945 . A determination is also made of the consciousness, step 929, or unconsciousness, step 915, (FIG. 9e) of the patient.

Whether the patient is conscious, step 929, or unconscious, step 915 (FIG. 9e), and an ALARM message is received by the central monitoring station, step 911, there are five alternatives which can help get the patient to the nearest Emergency Room. The Central Monitoring Station will suggest to the conscious patient that he/she go to the nearest Emergency Room, step 971 . The Central Monitoring Station calls EMS (emergency medical services) and asks EMS to transport the patient to the nearest Emergency Room, step 972 . The central Monitoring Station calls the patient's MD. The patient's doctor calls EMS and asks EMS to transport the patient to nearest Emergency Room, step 973 . A Good Samaritan discovers the patient, step 917, and calls EMS at 911 and asks EMS to transport the patient to the nearest Emergency Room, step 974 . The patient goes to the nearest Emergency Room, step 975 (FIG. 9f).

Recharge Base Station

FIG. 10 shows an embodiment of a recharge base station 1960 apparatus for the cellular telephone 1929, wrist monitor 1921 and pager 1931 . Recharge base station 1960 is typically connected to a 110 volt, 60 cycle, AC plug 1962, which powers the recharge base station 1960, and which, through step down transformers, not shown, recharges the batteries of the cellular telephone 1929 and wrist monitor 1921 . Of course the base station can be designed to handle any local voltage. A stand-by battery, not shown, within the recharge base station 1960 is available to power the land line telephone 1905, the cell phone 1929, and/or the pager 1931, should the AC power source be inoperative.

Should the wrist monitor 1921 worn by a patient, step 901, detect an ALARM condition 939, FIG. 9f, comatose condition 913, dying or dead condition 917, Hi/Lo HRV, ACRR 920 (FIG. 9d), MARR 923 (FIG. 9d), then the base station 1960, will first attempt to dial out, to the central monitoring station 911 (FIG. 9b), on the land line telephone 1905 .

Hi/Lo HRV, as indicated, is calculated based on the following parameters shown in diamond shaped decision tree boxes of FIG. 9d: SPS (step 925), AMo (step 927), DX (step 929), DX/M (step 931), Heart rate (HR) (step 933), Low HRV (step 935), and the total score ranges from +2.0 (caution)>+2.5 (alarm) (step 937). Negative output (parasympathetic) exits to the left of the diamond shaped decision tree boxes 925, 927, 929, 931, 933, 935, 937 with negative numbers, and positive output (sympathetic) exits to the right of the boxes with positive numbers. If after about fifteen to thirty seconds contact is not established with the central monitoring station, step 911, then the cellular telephone 1929, will call the central monitoring station, step 911, and report the ALARM condition. Should the cellular telephone 1929, make contact with the central monitoring station, step 911, then the pager 1931, will report an ALARM condition to the central monitoring station, step 911 . When the patient is outside the home then, with the exception of the land line telephone alternative 1905, the same protocol applies.

"Grab-the line" technology is installed so that if the land line hand set 1905 is being used or is off the hook, and ALARM message to the central monitoring station, step 911, can still be transmitted. "GRAB-THE-LINE" technology is supplied by the local telephone company and is used when an emergency exists. It interrupts a busy line to convey an emergency message.

When an ALARM is transmitted to the central monitoring station, step 911, the type of ALARM: comatose 913 (FIG. 9b), dying or dead 917 (FIG. 9b), Hi/Lo HRV (FIG. 9d), HR 933, Lo HRV 935, ACRR 920 (FIG. 9d), MARR 923 (FIG. 9d), is indicated to the central monitoring station, step 911.

Figure 11:
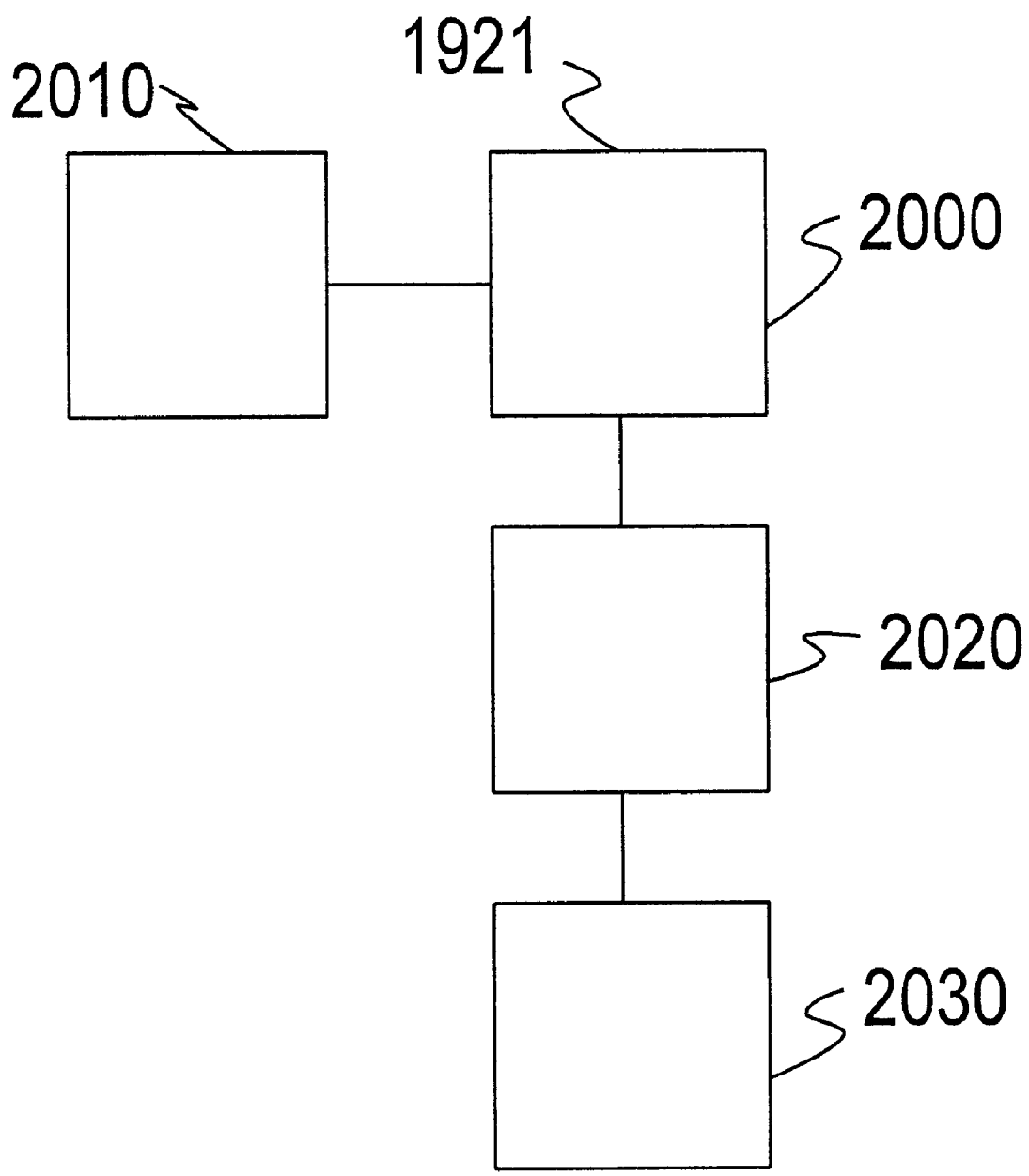
FIG. 11 shows a schematic diagram of the components of the wrist monitor.
Figure 12:
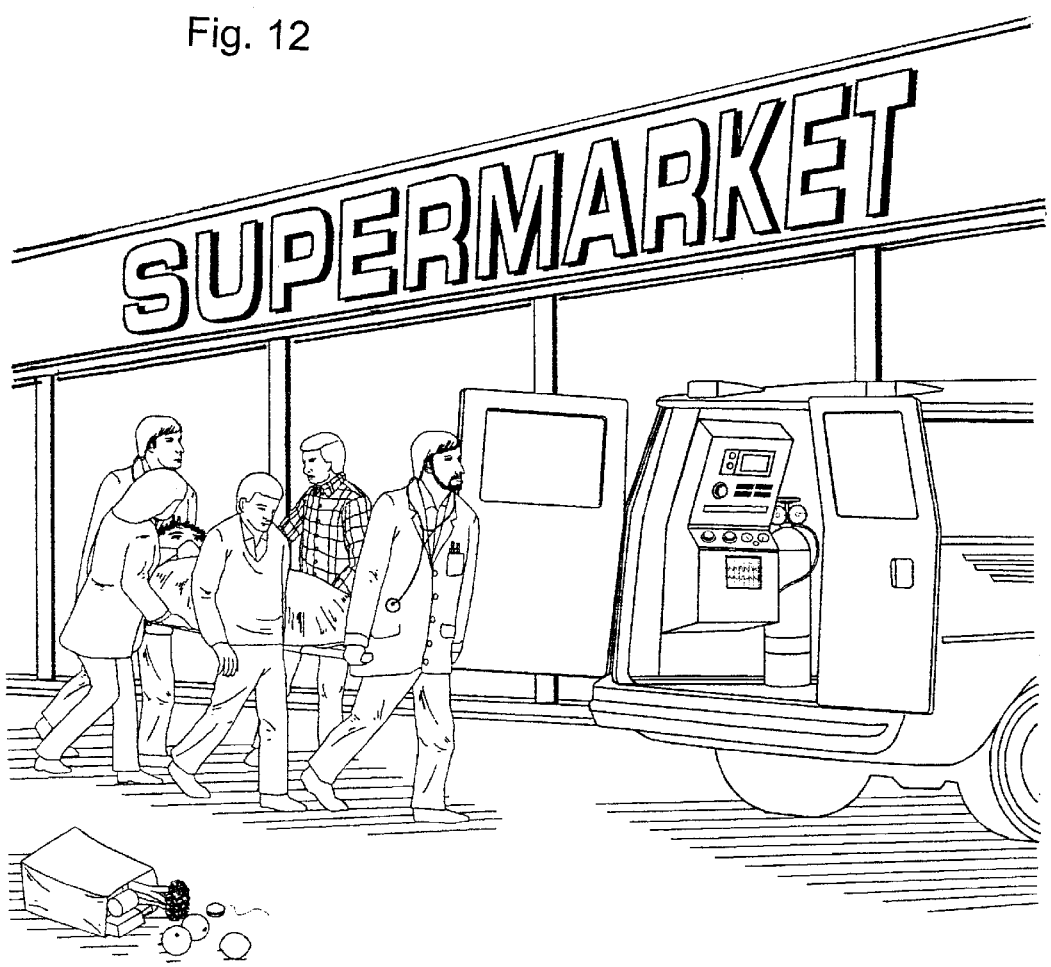
FIG. 12 shows an EMS vehicle and personnel rescuing a patient who may have experienced a Comatose ALARM, or a Heart Attack, or suffered an accident.

FIG. 11 schematically shows components of the wrist monitor 1921. The wrist monitor 1921 would include one or more sensor(s) 2010 for measuring Time Intervals and other parameters described above, a microprocessor 2000 for performing calculations of the present method, memory 2020 for storing information to perform the calculations or resulting from the calculations, and a radio transmitter for communicating with the base station components such as the land line, cellular telephone or pager (or the wrist monitor could include or be hard wired to a pager). The wrist monitor 1921 could also be provided with an audible alarm.

EXAMPLES

Example 1

TABLE 3 shows the parameters used in Example 1 on typical patient for whom sympathetic and parasympathetic parameters were measured and compared to absolute upper and lower limits.

TABLE 3

| General Preferences | |
|---|---|
| Code Version = v1.09i | Min Dx = 0.01 |
| Segment_size = 101 | Graphs/Hours = 24 |
| Resolution = 0.06 | Auto Pause = 0 |
| Cluster Min = 3 | |
| Baseline: 10–500 | |

TABLE 3-continued

```
Outliers = 3
Ectopic Min–Max = 0.75 -> 1.25
FlexType = 1
FlexStress = 0
FlexCoun = 3
FlexStress Count = 3
HRV STATUS                      Abs.Dx.Lo
Caution-Lo = -2.00              Caution-Lo = 0.06
Caution-Hi = 2.00               Caution-Tm = 10/50
Graph Avg = 1 pts               Graph Avg = 3 pts
Caution-Tm = 30.00              Alarm-Lo = 0.06
Use avg as val? yes             Shunt? no
Alarm-Lo = -2.50                Alarm-Tm = 15/50
Shunt? no
Alarm-Hi = 2.50
Alarm-Tm = 30.00
Abs.SPS.Hi                      Abs.Dx/Mdn.Hi
Caution-Hi = 48.00              Caution-Hi = 0.43
Caution-Tm = 5/50               Caution-Tm = 15/50
Graph Avg = 3 pts               Graph Avg = 3 pts
Alarm-Hi = 48.00                Alarm-Hi = 0.43
Shunt? no                       Shunt? no
Alarm-Tm = 15/50                Alarm-Tm = 20/50
Abs.SPS.Lo                      Abs.Dx/Mdn.Lo
Caution-Lo = 4.00               Caution-Lo = 0.02
Caution-Tm = 5/50               Caution-Tm = 5/50
Graph Avg = 3 pts               Graph Avg = 3 pts
Alarm-Hi = 4.00                 Alarm-Lo = 0.02
Shunt? no                       Shunt? no
Alarm-Tm = 10/50                Alarm-Tm = 15/50
Abs.AMo.Hi                      ACRR
Caution-Hi = 90.00              Caution-Lo = 0.85
Caution-Tm = 15/50              Caution-Hi = 50.00
Graph Avg = 3 pts               Graph Avg = 10 pts
Alarm-Hi = 90.00                Caution-Tm = 52.00
Shunt? no                       Use avg as val? no
Alarm-Tm = 20/50                Alarm-Lo = 0.85
                                Shunt? no
                                Alarm-Hi = 50.00
                                Alarm-Tm = 52.00
Abs.AMo.Lo                      Low HRV
Caution-Lo = 10.00              Caution-Lo = 45.00
Caution-Tm = 15/50              Caution-Hi = 1.10
Graph Avg = 3 pts               Graph Avg = 10 pts
Alarm-Lo = 10.00                Caution-Tm = 30.00
Shunt? no                       Use avg as val? yes
AlarmTm = 20/50                 Alarm-Lo = 0.85
                                Shunt? no
                                Alarm-Hi = 1.10
                                Alarm-Tm = 0.00
Abs.Dx.Hi                       Heart Rate
Caution-Hi = 0.50               Caution-Lo = 45.00
Caution-Tm = 5/50               Caution-Hi = 135.00
Graph Avg = 3 pts               Graph Avg = 3 pts
Alarm-Hi = 0.50                 Caution-Tm = 45.00
Shunt? no                       Use avg as val? yes
Alarm-Tm = 10/50                Alarm-Lo = 45.00
                                shunt? no
                                Alarm-Hi = 135.00
                                Alarm-Tm = 30.00
```

It should be apparent that embodiments other than the above-described come within the spirit and scope of the present invention. Hence, the present invention is not limited by the above disclosure, but rather, is defined by the claims appended hereto.

What is claimed is:

1. A method of predicting arrhythmia in a person comprising the steps of:

measuring the heart rate of the person, analyzing the measured heart rate to determine a value for at least one marker for Heart Rate Variability; and comparing the determined value with both a standard predetermined upper limit and a standard predetermined lower limit for the at least one marker, the upper limit indicates decreased variability, and the lower limit indicates increased variability, the at least one marker including at least one parameter of sympathetic or parasympathetic activity.

2. The method of claim 1, wherein the at least one marker comprises at least one parameter selected from the group consisting of Abs.SPS, Abs.AMo, Abs.DX, Abs.DX/M, and Abs.FWHM, Abs.SDANN, Abs.AM, Abs.ANN, and determining the at least one marker occurs over a Time Segment comprising about 25 to about 501 Time Intervals.

3. The method of claim 2, wherein the at least one marker comprises Abs.SPS (Absolute Sympathetic Parasympathetic Stress), wherein, for ambulatory patients age 18 to 54, the upper limit is about 48, and further comprising signaling a Caution if the value for Abs.SPS is determined as greater than or equal to the upper limit for a ratio of at least about 5 out of 50 Time Segments, and signaling an ALARM if the value for Abs.SPS is determined as greater than or equal to the upper limit for a ratio of at least about 30 out of 50 Time Segments, wherein at least about 30 Time Segments are measured, and the lower limit is about 2.5 and further comprising signaling a Caution if the value for Abs.SPS is determined as less than or equal to the lower limit for a ratio of at least about 15 out of 50 Time Segments, and signaling an ALARM if the value for Abs.SPS is determined as less than or equal to the lower limit for a ratio of at least about 25 out of 50 Time Segments, wherein at least about 30 Time Segments are measured.

4. The method of claim 2, wherein the at least one marker comprises Abs.AMo (Absolute Amplitude of the Mode), wherein, for ambulatory patients age 18 to 54, the upper limit is about 90 and further comprising signaling a Caution if the value for Abs.AMo is determined as greater than or equal to the upper limit for a ratio of at least about 15 out of 50 Time Segments, and signaling an ALARM if the value for Abs.AMo is determined as greater than or equal to the upper limit for a ratio of at least about 30 out of 50 Time Segments, wherein at least about 30 Time Segments are measured; and the lower limit is 10, and further comprising signaling a Caution if the value for Abs.AMo is determined as less than or equal to the lower limit for a ratio of at least about 15 out of 50 Time Segments, and signaling an ALARM if the value for Abs.AMo is determined as less than or equal to the lower limit for a ratio of at least about 25 out of 50 Time Segments, wherein at least about 30 Time Segments are measured.

5. The method of claim 2, wherein the at least one marker comprises Abs.DX (Absolute Delta X)

wherein, for ambulatory patients age 18 to 54, the upper limit is about 0.50 and further comprising signaling a Caution if the value for Abs.DX is determined as greater than or equal to the upper limit for a ratio of at least about 15 out of 50 Time Segments, and signaling an ALARM if the value for Abs.DX is determined as greater than or equal to the upper limit for a ratio of at least about 30 out of 50 Time Segments, wherein at least about 30 Time Segments are measured; and the lower limit is about 0.06 and further comprising signaling a Caution if the value for Abs.DX is determined as less than or equal to the lower limit for a ratio of at least about 10 out of 50 Time Segments, and signaling an ALARM if the value for Abs.DX is determined as less than or equal to the lower limit for a ratio of at least about 25 out of 50 time Segments, wherein at least about 30 Time Segments are measured.

6. The method of claim 2, wherein the at least one marker comprises Abs.DX/M (Absolute Delta X divided by the Median), wherein, for ambulatory patients age 18 to 54, the upper limit is about 0.425 and further comprising signaling a Caution if the value for Abs.DX/M is determined as greater than or equal to the upper limit for a ratio of at least about 15 out of 50 Time Segments, and signaling an ALARM if the value for Abs.DX/M is determined as greater than or equal to the upper limit for a ratio of at least about 25 out of 50 Time Segments, wherein at least about 30 Time Segments are measured; and the lower limit Caution is about 0.02, further comprising signaling a Caution if the value for Abs.DX/M is determined as less than or equal to the lower limit for a ratio of at least about 5 out of 50 Time Segments, and signaling an ALARM if the value for Abs.DX/M is determined as less than or equal to the lower limit for a ratio of at least about 25 out of 50 Time Segments, wherein at least about 30 Time Segments are measured.

7. The method of claim 2, wherein the at least one marker comprises Abs.SPS (Absolute Sympathetic Parasympathetic Stress), wherein, for ambulatory patients age 18 to 54, the upper limit is about 45 to about 50, and further comprising signaling a Caution if the value for Abs.SPS is determined as greater than or equal to the upper limit for a ratio of at least about 4 to about 6 out of 50 Time Segments, and signaling an ALARM if the value for Abs.SPS is determined as greater than or equal to the upper limit for a ratio of at least about 28 to about 32 out of 50 Time Segments, wherein at least about 30 Time Segments are measured and the lower limit is about 2.5 and further comprising signaling a Caution if the value for Abs.SPS is determined as less than or equal to the lower limit for a ratio of at least about 13 to 17 out of 50 Time Segments, and signaling an ALARM if the value for Abs.SPS is determined as less than or equal to the lower limit for a ratio of at least about 23–27 out of 50 Time Segments, wherein at least about 30 Time Segments are measured.

8. The method of claim 1, wherein the at least one marker comprises at least one parameter selected from the group consisting of PNN50, ACRR and MARR.

9. The method of claim 1, wherein HRV Status points are assigned as relative values as follows:

a) Caution equals –0.5 points or +0.5 points
b) ALARM equals –1 point or +1 point
c) Low HRV Caution and ALARM equals two and one half points
d) ACRR Caution and ALARM equals two and one half points
e) Low or High Heart Rate ALARM equals two and one half points
f) MARR ALARM equals two and one half points;
a combined total of all points generated, which equals between –1.99 and +1.99 points or less is an OK status;
a combined total of all points generated, which equals from about –2.0 to –2.49 or equals from about +2.0 to +2.49 points is a Caution status;
a combined total of all points generated, which equals about –2.5 points or less or equals about +2.5 points or more is a ALARM status.

10. The method of claim 1, wherein the at least one parameter is low-HRV, and further comprising signaling a low-HRV status Alarm if in a Time Segment a maximum Time Interval variation of about 0.62 seconds or lower is determined, with no more than two Time Segments having a Time Interval variation of above about 0.62 seconds, per about 100 or more Time Segments.

11. The method of claim 1, wherein the at least one parameter comprises ACRR Time Intervals, ACRR Time Intervals being Time Intervals between consecutive heart beats which are 25% less or 25% more than the previous Time Interval, and further comprising signaling an HRV Status Alarm if more than 50 minutes of ACRR Time Intervals are measured with no more than two consecutive Time Intervals which did not qualify as an ACRR Time Interval.

12. The method of claim 11, wherein an ACRR interval has a duration of 1>74 or 126>169 milliseconds.

13. The method of claim 1, further comprising signaling an HRV Status ALARM if the at least one parameter comprises MARR Time Intervals, MARR Time Intervals being a condition when a current pulse wave peak is preceded by about 5 to about 15 hundredths of a second by a preceding pulse wave peak, and the current peak is 25% to 90% less or 25% to 200% more than said preceding peak, and at least five minutes of said MARR Time Intervals are measured and there are no more than three consecutive Time Intervals which did not qualify as a MARR Time Segment during the time the at least five minutes was measured.

14. The method of claim 13, wherein an MARR interval has a duration of 0 or $\geqq$170 milliseconds.

15. The method of claim 1, wherein the at least one marker comprises Abs.SPS (Absolute Sympathetic Parasympathetic Stress), wherein, for ambulatory patients of age 55+, the upper limit is about 48, and further comprising signaling a Caution if the value for Abs.SPS is determined as greater than or equal to the upper limit for a ratio of at least about 10 out of 50 Time Segments, and signaling an ALARM if the value for Abs.SPS is determined as greater than or equal to the upper limit for a ratio of at least about 15 out of 50 Time Segments and at least about 30 Time Segments are measured, and the lower limit is about 4 and further comprising signaling a Caution if the value for Abs.SPS is determined as less than or equal to the lower limit for a ratio of at least about 10 out of 50 Time Segments, and signaling an ALARM if the value for Abs.SPS is determined as less than or equal to the lower limit for a ratio of at least about 15 out of 50 Time Segments, wherein at least about 30 Time Segments are measured.

16. The method of claim 1, wherein the at least one marker comprises Abs.AMo (Absolute Amplitude of the Mode), wherein, for ambulatory patients age 55+, the upper limit is about 90 and further comprising signaling a Caution if the value for Abs.AMo is determined as greater than or equal to the upper limit for a ratio of at least about 10 out of 50 Time Segments, and signaling an ALARM if the value for Abs.AMo is determined as greater than or equal to the upper limit for a ratio of at least about 15 out of 50 Time Segments, wherein at least about 30 Time Segments are measured; and the lower limit is about 10, and further comprising signaling a Caution if the value for Abs.AMo is determined as less than or equal to the lower limit for a ratio of at least about 15 out of 50 Time Segments, and signaling an ALARM if the value for Abs.AMo is determined as less than or equal to the lower limit for a ratio of at least about 20 out of 50 Time Segments, wherein at least about 30 Time Segments are measured.

17. The method of claim 1, wherein the at least one marker comprises Abs.DX (Absolute Delta X)

wherein, for ambulatory patients age 55+, the upper limit is about 0.50 and further comprising signaling a Caution if the value for Abs.DX is determined as greater than or equal to the upper limit for a ratio of at least about 10 out of 50 Time Segments, and signaling an ALARM if the value for Abs.DX is determined as greater than or equal to the upper limit for a ratio of at least about 15 out of 50 Time Segments, wherein at least about 30 Time Segments are measured; and the lower limit is about 0.06 and further comprising signaling a Caution if the value for Abs.DX is determined as less than or equal to the lower limit for a ratio of at least about 15 out of 50 Time Segments, and signaling an ALARM if the value for Abs.DX is determined as less than or equal to the lower limit for a ratio of at least about 20 out of 50 time Segments, wherein at least about 30 Time Segments are measured.

18. The method of claim 1, wherein the at least one marker comprises Abs.DX/M (Absolute Delta X divided by the Median), wherein, for ambulatory patients age 55+, the upper limit is about 0.425 and further comprising signaling a Caution if the value for Abs.DX/M is determined as greater than or equal to the upper limit for a ratio of at least about 15 out of 50 consecutive Time Segments, and signaling an ALARM if the value for Abs.DX/M is determined as greater than or equal to the upper limit for a ratio of at least about 20 out of 50 Time Segments, wherein at least about 30 Time Segments are measured; and the lower limit Caution is about 0.02, further comprising signaling a Caution if the value for Abs.DX/M is determined as less than or equal to the lower limit for a ratio of at least about 5 out of 50 Time Segments, and signaling an ALARM if the value for Abs.DX/M is determined as less than or equal to the lower limit for a ratio of at least about 15 out of 50 Time Segments, wherein at least about 30 Time Segments are measured.

19. The method of claim 1, further comprising the step of providing the patient with a wrist monitor, and a communication system comprising at least one member of the group consisting of a phone for communicating with a land line, a cellular telephone, and a pager, wherein the at least one marker comprises at least one member of the group consisting of Abs.SPS, Abs.AMo, Abs.DX, Abs.DX/M, and Abs.FWHM, Abs.SDANN, Abs.AM, Abs.ANN, Heart Rate, Low HRV, and ACRR, and comprising said measuring of the heart rate of the person by measuring pulse with the wrist monitor during at least one Time Segment and calculating Points with the wrist monitor for the at least one marker based on the measurement of the heart rate during the at least one Time Segment, and then summing and storing the points with the wrist monitor thereby creating an HRV Status report, the wrist monitor comprising a microprocessor programed for said calculating and summing, and having memory for said storing.

20. The method of claim 19, wherein if a sufficient number of points are calculated and summed the HRV Status report detects an HRV ALARM condition, if the HRV ALARM condition is detected in the HRV Status report, then the patient's communication system will first try to communicate with the land line to make a connection with a central monitoring station, and failing to make a connection with the central monitoring station the patient's communication system will then try to communicate with the central monitoring station using at least one member of the group consisting of the cellular telephone and the pager, if the communication system is unable to connect to the central monitoring station after about at least 10 minutes, the wrist monitor will trigger at least one alarm selected from the group consisting of: (1) a flashing red light, (2) vibration, and (3) a pre-recorded voice message suggesting that an HRV Status ALARM condition has been detected, and to please go to the nearest Emergency Room.

21. The method of claim 1, wherein the at least one marker comprises at least two parameters selected from the group consisting of Abs.SPS, Abs.AMo, Abs.DX, Abs.DX/M, and Abs.FWHM, Abs.SDANN, Abs.AM, Abs.ANN, Heart Rate, Low HRV, and ACRR determined over a Time Segment comprised of about 25 to about 501 Time Intervals.

22. The method of claim 1, wherein the at least one marker comprises at least three parameters selected from the group consisting of Abs.SPS, Abs.AMo, Abs.DX, Abs.DX/M, and Abs.FWHM, Abs.SDANN, Abs.AM, Abs.ANN, Heart Rate, Low HRV, and ACRR determined over a Time Segment comprised of about 25 to 501 Time Intervals.

23. The method of claim 1, wherein the at least one marker comprises Abs.AMo (Absolute Amplitude of the Mode), wherein, for ambulatory patients age 18 to 54, the upper limit is about 85 to 95 and further comprising signaling a Caution if the value for Abs.AMo is determined as greater than or equal to the upper limit for a ratio of at least about 13 to 17 out of 50 Time Segments, and signaling an ALARM if the value for Abs.AMo is determined as greater than or equal to the upper limit for a ratio of at least about 28 to 32 out of 50 Time Segments, wherein at least about 30 Time Segments are measured; and the lower limit is 8 to 12, and further comprising signaling a Caution if the value for Abs.AMo is determined as less than or equal to the lower limit for a ratio of at least about 13 to 17 out of 50 Time Segments, and signaling an ALARM if the value for Abs.AMo is determined as less than or equal to the lower limit for a ratio of at least about 23 to 27 out of 50 Time Segments, wherein at least about 30 Time Segments are measured.

24. The method of claim 1, wherein the at least one marker comprises Abs.DX (Absolute Delta X)

wherein, for ambulatory patients age 18 to 54, the upper limit is about 0.4 to about 0.6 and further comprising signaling a Caution if the value for Abs.DX is determined as greater than or equal to the upper limit for a ratio of at least about 13 to about 17 out of 50 Time Segments, and signaling an ALARM if the value for Abs.DX is determined as greater than or equal to the upper limit for a ratio of at least about 28 to about 32 out of 50 Time Segments, wherein at least about 30 Time Segments are measured; and the lower limit is about 0.05 to about 0.07 and further comprising signaling a Caution if the value for Abs.DX is determined as less than or equal to the lower limit for a ratio of at least about 8 to about 12 out of 50 Time Segments, and signaling an ALARM if the value for Abs.DX is determined as less than or equal to the lower limit for a ratio of at least about 23 to about 27 out of 50 Time Segments, wherein at least about 30 Time Segments are measured.

25. The method of claim 1, wherein the at least one marker comprises Abs.DX/M (Absolute Delta X divided by the Median), wherein, for ambulatory patients age 18 to 54, the upper limit is about 0.4 to 0.5 and further comprising signaling a Caution if the value for Abs.DX/M is determined as greater than or equal to the upper limit for a ratio of at least about 13 to about 17 out of 50 Time Segments, and signaling an ALARM if the value for Abs.DX/M is determined as greater than or equal to the upper limit for a ratio of at least about 23 to 27 out of 50 Time Segments, wherein at least about 30 Time Segments are measured; and the lower limit Caution is about 0.015 to 0.025, further comprising signaling a Caution if the value for Abs.DX/M is determined as less than or equal to the lower limit for a ratio of at least about 4 to 6 out of 50 Time Segments, and signaling an ALARM if the value for Abs.DX/M is determined as less than or equal to the lower limit for a ratio of at least about 23 to 27 out of 50 Time Segments, wherein at least about 30 Time Segments are measured.

26. The method of claim 1, wherein RR time intervals are measured and normal intervals (NN) are 75>125 milliseconds, ACRR intervals are 1>74 and 126>169 milliseconds, and MARR intervals are 0 and 170+ milliseconds.

27. The method of claim 1, wherein the at least one marker comprises kurtosis ($a_4$)

wherein, for ambulatory patients age 18 to 54, further comprising signaling an Increased HRV DX ALARM if the value of kurtosis ($a_4$) is $\geq 30$ for a ratio of at least about 28 to 31 out of 50 Time Segments, wherein at least about 30 Time Segments are measured; and signaling an Decreased HRV DX ALARM if the value for kurtosis ($a_4$) is $\leq 0.3$ for at least about 23 to 26 out of 50 Time Segments, wherein at least about 30 Time Segments are measured.

28. The method of claim 1, wherein the at least one marker comprises Abs.SPS (Absolute Sympathetic Parasympathetic Stress), wherein, for ambulatory patients of age 55+, the upper limit is about 48±4.8, and further comprising signaling a Caution if the value for Abs.SPS is determined as greater than or equal to the upper limit for a ratio of at least about 10±2 out of 50 Time Segments, and signaling an ALARM if the value for Abs.SPS is determined as greater than or equal to the upper limit for a ratio of at least about 15±2 out of 50 Time Segments and at least about 30 Time Segments are measured, and the lower limit is about 4±0.4 and further comprising signaling a Caution if the value for Abs.SPS is determined as less than or equal to the lower limit for a ratio of at least about 10±2 out of 50 Time Segments, and signaling an ALARM if the value for Abs.SPS is determined as less than or equal to the lower limit for a ratio of at least about 15±2 out of 50 Time Segments, wherein at least about 30 Time Segments are measured.

29. The method of claim 1, wherein the at least one marker comprises Abs.AMo (Absolute Amplitude of the Mode), wherein, for ambulatory patients age 55+, the upper limit is about 90±9 and further comprising signaling a Caution if the value for Abs.AMo is determined as greater than or equal to the upper limit for a ratio of at least about 10±2 out of 50 Time Segments, and signaling an ALARM if the value for Abs.AMo is determined as greater than or equal to the upper limit for a ratio of at least about 15±2 out of 50 Time Segments, wherein at least about 30 Time Segments are measured; and the lower limits about 10±1, and further comprising signaling a Caution if the value for Abs.AMo is determined as less than or equal to the lower limit for a ratio of at least about 15±2 out of 50 Time Segments, and signaling an ALARM if the value for Abs.AMo is determined as less than or equal to the lower limit for a ratio of at least about 20±2 out of 50 Time Segments, wherein at least about 30 Time Segments are measured.

30. The method of claim 1, wherein the at least one marker comprises Abs.DX (Absolute Delta X)

wherein, for ambulatory patients age 55+, the upper limit is about 0.50±0.05 and further comprising signaling a Caution if the value for Abs.DX is determined as greater than or equal to the upper limit for a ratio of at least about 10±2 out of 50 Time Segments, and signaling an ALARM if the value for Abs.DX is determined as greater than or equal to the upper limit for a ratio of at least about 15±2 out of 50 Time Segments, wherein at least about 30 Time Segments are measured; and the lower limit is about 0.06±0.006 and further comprising signaling a Caution if the value for Abs.DX is determined as less than or equal to the lower limit for a ratio of at least about 15±2 out of 50 Time Segments, and signaling an ALARM if the value for Abs.DX is determined as less than or equal to the lower limit for a ratio of at least about 20±2 out of 50 time Segments, wherein at least about 30 Time Segments are measured.

31. The method of claim 1, wherein the at least one marker comprises Abs.DX/M (Absolute Delta X divided by the Median), wherein, for ambulatory patients age 55+, the upper limit is about 0.425±0.0425 and further comprising signaling a Caution if the value for Abs.DX/M is determined as greater than or equal to the upper limit for a ratio of at least about 15±2 out of 50 consecutive Time Segments, and signaling an ALARM if the value for Abs.DX/M is determined as greater than or equal to the upper limit for a ratio of at least about 20±2 out of 50 Time Segments, wherein at least about 30 Time Segments are measured; and the lower limit Caution is about 0.02±0.002, further comprising signaling a Caution if the value for Abs.DX/M is determined as less than or equal to the lower limit for a ratio of at least about 5±1 out of 50 Time Segments, and signaling an ALARM if the value for Abs.DX/M is determined as less than or equal to the lower limit for a ratio of at least about 15±2 out of 50 Time Segments, wherein at least about 30 Time Segments are measured.

32. An apparatus comprising,
a wrist monitor, said wrist monitor comprising a microprocessor, memory, a motion detector and an RF transmitter, and
a communication system comprising at least one member of the group consisting of a phone for communicating with a land line, a cellular telephone, and a pager,
said wrist monitor comprising a microprocessor programmed to perform the method of claim 1.

33. An apparatus for predicting arrhythmia in a person, comprising,
a wrist monitor for:
measuring the heart rate of the person,
analyzing the measured heart rate to determine a value for at least one marker for Heart Rate Variability; and
comparing the determined value with both a standard predetermined upper limit and a standard predetermined lower limit for the at least one marker, the upper limit indicates decreased variability, and the lower limit indicates increased variability, the at least one marker including at least one parameter of sympathetic or parasympathetic activity, said wrist monitor comprising a microprocessor, memory, a motion detector and an RF transmitter, and
a communication system comprising at least one member of the group consisting of a phone for communicating with a land line, a cellular telephone, and a pager,
wherein the at least one marker comprises at least one member selected from the group consisting of Abs.SPS, Abs.AMo, Abs.DX, Abs.DX/M, and Abs.FWHM, Abs.SDANN, Abs.AM, Abs.ANN,Heart Rate, Low HRV, and ACRR, determined over a Time Segment comprising about 25 to about 501 Time Intervals and Points are calculated for the Time Segment, then summed and stored creating an HRV Status report by the wrist monitor, the wrist monitor comprising a microprocessor programed to make said calculations and summing, and memory for said storing.

34. The apparatus of claim 33, wherein said RF transmitter is capable of communicating with at least one member of the group consisting of a cellular telephone and a pager.

35. An apparatus for predicting arrhythmia in a person, comprising,
a wrist monitor for:
measuring the heart rate of the person,
analyzing the measured heart rate to determine a value for at least one marker for Heart Rate Variability; and
comparing the determined value with both a standard predetermined upper limit and a standard predetermined lower limit for the at least one marker, the upper limit indicates decreased variability, and the lower limit indicates increased variability, the at least one marker including at least one parameter of sympathetic or parasympathetic activity, and
a communication system comprising a phone for communicating with a land line, a cellular telephone, and a pager,
wherein the at least one marker comprises at least one member selected from the group consisting of Abs.SPS, Abs.AMo, Abs.DX, Abs.DX/M, and Abs.FWHM, Abs.SDANN, Abs.AM, Abs.ANN,Heart Rate, Low HRV, and ACRR, determined over a Time Segment comprising about 25 to about 501 Time Intervals and Points and are calculated for the Time Segment, then summed and stored creating an HRV Status report by the wrist monitor, the wrist monitor comprising a microprocessor programed to make said calculations and summing, and memory for said storing.

36. The apparatus of claim 35, wherein if an HRV ALARM condition is detected in the HRV Status report, then the patient's communication system will first try its land line to make a connection with the central monitoring station, and failing to make a connection with the central monitoring station will then try to communicate with the central monitoring station using at least one member of the group consisting of the cellular telephone and the pager, if the communication system is unable to connect to the central monitoring station after about at least 10 minutes, the wrist monitor will trigger at least one alarm selected from the group consisting of (1) a flashing red light, (2) vibration, and (3) a pre-recorded voice message suggesting that an HRV Status ALARM condition has been detected, and to please go to the nearest Emergency Room.

37. An apparatus comprising,
a wrist monitor, said wrist monitor comprising a microprocessor, memory, and a Time Interval sensor, and
said microprocessor programmed to perform the method of claim 1.

38. A method for regulating heart rate comprising having a pacemaker implanted in a human induce variation into the human's heart rate, such that, when the breathing rate is in the range of 24 to 27 breaths per minute or more, the pacing rate would range from about 0.5 to about 0.42 seconds over a predetermined time segment.

39. A pacemaker for implanting in a human programmed to induce variation into the human's heart rate, such that, when the breathing rate is in the range of 24 to 27 breaths per minute or more, the pacing rate would range from about 0.5 to about 0.42 seconds over a predetermined time segment.

40. The pacemaker of claim 39, wherein the pacemaker is an impedance pacemaker and is programmed to provide the heart rate variability based on a record of the patient's heart rate variability based on a record of the patient's heart rate variability.

41. The pacemaker of claim 39, wherein the pacemaker is an impedance pacemaker and is programmed to provide the heart rate variability based on a record of the patient's heart rate variability based on a record of heart rate variability of an individual most nearly matching the patient's age, sex, race, build and athletic condition.

42. The pacemaker of claim 39, wherein the pacemaker is an impedance pacemaker and is programmed to provide the heart rate variability based on a record of the patient's heart rate variability based on a random pulse rate generator.

* * * * *